(12) United States Patent
Masubuchi et al.

(10) Patent No.: US 8,901,265 B2
(45) Date of Patent: Dec. 2, 2014

(54) CATIONIC (METH) ACRYLIC SILICONE-BASED GRAFT COPOLYMER AND COSMETIC CONTAINING SAME

(75) Inventors: Yuji Masubuchi, Tokyo (JP); Kazuhiro Suzuki, Tokyo (JP); Emi Akabane, Gunma (JP)

(73) Assignees: Kose Corporation, Tokyo (JP); Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/007,521

(22) PCT Filed: Mar. 29, 2012

(86) PCT No.: PCT/JP2012/002170
§ 371 (c)(1),
(2), (4) Date: Sep. 25, 2013

(87) PCT Pub. No.: WO2012/132444
PCT Pub. Date: Oct. 4, 2012

(65) Prior Publication Data
US 2014/0018508 A1    Jan. 16, 2014

(30) Foreign Application Priority Data
Mar. 31, 2011    (JP) .................................. 2011-079696

(51) Int. Cl.
| | | |
|---|---|---|
| *C08F 30/08* | (2006.01) | |
| *A61K 8/898* | (2006.01) | |
| *A61Q 5/06* | (2006.01) | |
| *C08F 290/06* | (2006.01) | |
| *A61Q 1/02* | (2006.01) | |
| *A61Q 1/06* | (2006.01) | |
| *A61Q 1/10* | (2006.01) | |
| *A61Q 1/12* | (2006.01) | |
| *A61Q 5/00* | (2006.01) | |
| *A61Q 5/02* | (2006.01) | |
| *A61Q 17/04* | (2006.01) | |
| *A61Q 19/00* | (2006.01) | |
| *A61Q 19/10* | (2006.01) | |

(52) U.S. Cl.
CPC . *A61K 8/898* (2013.01); *A61Q 5/06* (2013.01); *C08F 290/068* (2013.01); *A61Q 1/02* (2013.01); *A61Q 1/06* (2013.01); *A61Q 1/10* (2013.01); *A61Q 1/12* (2013.01); *A61Q 5/002* (2013.01); *A61Q 5/02* (2013.01); *A61Q 17/04* (2013.01); *A61Q 19/00* (2013.01); *A61Q 19/10* (2013.01)
USPC .................... 526/279; 424/70.122; 424/70.12

(58) Field of Classification Search
USPC ............................ 526/279; 424/70.122, 70.12
See application file for complete search history.

(56) References Cited

U.S. PATENT DOCUMENTS

| | | | | |
|---|---|---|---|---|
| 5,166,276 A | * | 11/1992 | Hayama et al. ............. | 525/329.7 |
| 5,229,435 A | * | 7/1993 | Sakai et al. .................... | 523/105 |
| 5,622,694 A | * | 4/1997 | Torgerson et al. ........ | 424/70.122 |
| 5,760,136 A | * | 6/1998 | Kato et al. ..................... | 525/100 |
| 8,524,849 B2 | * | 9/2013 | Stark ............................... | 528/32 |
| 2009/0104238 A1 | * | 4/2009 | Stark et al. .................... | 424/401 |

FOREIGN PATENT DOCUMENTS

| | | |
|---|---|---|
| JP | 04-359914 | 12/1992 |
| JP | 5-924 | 1/1993 |
| JP | 05-017324 | 1/1993 |

(Continued)

*Primary Examiner* — Margaret Moore
(74) *Attorney, Agent, or Firm* — Occhiuti & Rohlicek LLP

(57) ABSTRACT

The present invention provides a novel (meth)acrylic silicone-based graft copolymer that is preferably used for cosmetics and the like. The (meth)acrylic silicone-based graft copolymer of the present invention is a copolymer obtained by reacting the following radically polymerizable monomers (a) to (d):
  (a) a compound represented by the following general formula (I);
  (b) at least one selected from a compound represented by the following general formula (II) and a compound represented by the following formula (III);
  (c) a compound represented by the following general formula (IV); and
  (d) a compound represented by the following general formula (V), wherein
the copolymer is dissolved at a level of 50 mass % or more in 99.5% ethanol at 25° C.

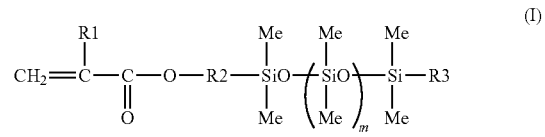

(I)

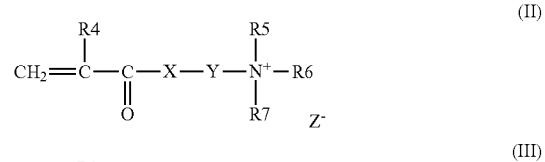

(II)

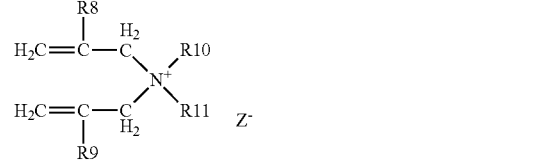

(III)

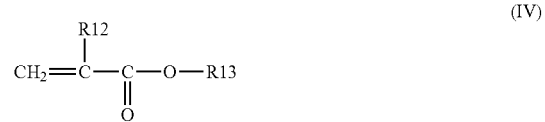

(IV)

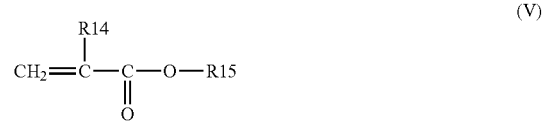

(V)

6 Claims, No Drawings

(56) References Cited

FOREIGN PATENT DOCUMENTS

| | | |
|---|---|---|
| JP | 07-224127 | 8/1995 |
| JP | 2704730 | 10/1997 |
| JP | 2002-265321 | 9/2002 |
| JP | 2003-34784 | 2/2003 |
| JP | 4246022 | 1/2009 |
| JP | 2009-529562 | 8/2009 |
| JP | 2010-518190 | 5/2010 |
| WO | 2007/104645 | 9/2007 |
| WO | 2008/095822 | 8/2008 |

* cited by examiner

CATIONIC (METH)ACRYLIC SILICONE-BASED GRAFT COPOLYMER AND COSMETIC CONTAINING SAME

CROSS-REFERENCE TO RELATED APPLICATIONS

This application is a National Stage of International Application No. PCT/JP2012/002170 filed on Mar. 29, 2012, which claims priority to Japanese Application No. 2011-079696 filed Mar. 31, 2011, the contents of which are hereby incorporated by reference in their entirety.

TECHNICAL FIELD

The present invention relates to a novel cationic (meth)acrylic silicone-based graft copolymer and a cosmetic containing the same. More specifically, the present invention relates to a cationic (meth)acrylic silicone-based graft copolymer that is particularly suitable for out-bath type hair cosmetics and the like.

BACKGROUND ART

Since (meth)acrylic polymer is transparent and it forms a film and has good workability, it has been widely used as a coating material, an adhesive material, a material for ink, a material for external use on skin, a cosmetic material, etc. However, since acrylic resin has high polarity, it has also had many problems. As such, various copolymers have been developed so far. Examples of the thus developed copolymers include: an acryl-silicone-based graft copolymer obtained by radical copolymerization of a dimethylpolysiloxane compound having a radically polymerizable group at one end of a molecular chain thereof and a radically polymerizable monomer having acrylate and/or methacrylate as a main body (see for example, Patent Document 3); and an amphiphilic block copolymer comprising a polysiloxane block and a cationic block (see for example, Patent Document 2).

Meanwhile, there are various types of cosmetics. Specific examples of a leave-in type hair cosmetic that intends to be mainly used out of the bath include styling spray, styling mousse, hair mist, hair wax, hair gel, hair oil, and hair treatment.

In recent years, with regard to such out-bath type hair cosmetics, there has been an increasing demand for a hair styling product capable of rearranging hair without flaking, thereby easily arranging hair style, a hair conditioner for dry hair, a hair styling product for thinning hair, and the like. As a result, with regard to a hair styling product, it has been desired to develop a non-sticky elastic resin so as to allow hairs to softly adhere to one another without fixing them strongly to impart voluminousness and airly feeling from hair roots, or so as to impart the bounce and resilience of healthy hair to damaged hair. In addition, with regard to a hair conditioner, it has been desired to develop a resin having high affinity for silicone as a conditioning ingredient for the repair of hair surface and the improvement of the touch.

In order to meet these needs, various types of resins have been developed. For some examples, there are the silicone-based copolymers described in above-mentioned patent documents.

For example, Patent Document 1 describes a silicone copolymer consisting of: 0.1% to 40% one or more silicone macromonomers having the following general formula (1):

$$R^1R^2SiO(SiR_2O)_nSiR_2R^1 \quad (1)$$

[wherein R represents monovalent, linear or cyclic, and Si—C-bound or optionally substituted hydrocarbon groups, which are independent from one another, or alkoxy groups each having 1 to 18 carbon atoms; $R^1$ represents a polymerizable group; and n represents 10 to 1000]; B) 0.5% to 10% radically polymerizable carboxylic acid selected from the group consisting of crotonic acid and acrylic acid, and optionally further containing other hydrophilic monomers; and C) 30% to 99.4% hydrophobic monomer comprising vinyl acetate and optionally further comprising other hydrophobic monomers.

Moreover, Patent Document 2 describes an amphiphilic block copolymer comprising a) at least one siloxane block polymer represented by the following formula (I):

(wherein $R_1$ and $R_2$ each independently represent an alkyl group, an alkoxy group, a phenylalkyl group, an aryl group, an aryloxy group, an alkylaryl group, an alkylamine group, an alkylhydroxy group, a polyoxyalkylene group, or a polyalkylenepolyamine group; and n represents a number between 2 and 10,000), and b) a cationic block polymer formed with at least one cationic monomer represented by the following formula (II):

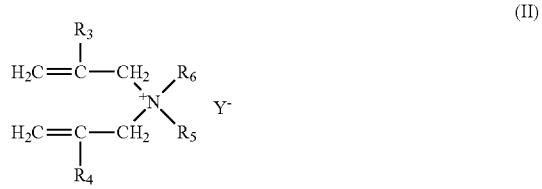

(wherein $R_3$ and $R_4$ each independently represent a hydrogen atom or an alkyl group containing 1 to 4 carbon atoms; $R_5$ and $R_6$ each independently represent a hydrogen atom, or an alkyl group, a hydroxyalkyl group, a carboxyalkyl group, a carboxyamidealkyl group or an alkoxyalkyl group, which contains 1 to 18 carbon atoms; and $Y^-$ represents an anion).

However, these silicone-based copolymers have not sufficiently satisfied the aforementioned needs.

In addition to the aforementioned patent documents, the following publications describe a copolymer that can be used as a cosmetic, a hair wash, or the like, which has a repeating unit that is partially the same as that of the cationic (meth) acrylic silicone-based graft copolymer according to the present invention. Nevertheless, none of such publications describe the same copolymer as that of the present invention.

(Patent Document 3)

An acryl-silicone-based graft copolymer obtained by radical copolymerization of a dimethylpolysiloxane compound having a radically polymerizable group at one end of a molecular chain thereof, represented by the following general formula (1):

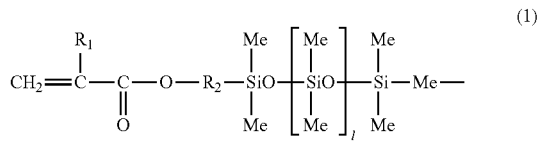

and a radically polymerizable monomer comprising, as a main body, acrylate and/or methacrylate.
(Patent Document 4)

A cationic graft (co)polymer obtained by polymerization of a macromonomer comprising, as essential components,
(A) at least one monomer unit having a cationic group represented by the following general formula (I):

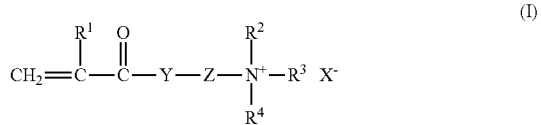

or the following formula (II):

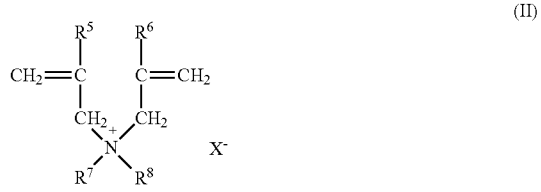

and
(B) at least one monomer unit having a nonionic group represented by the following formula (III):

or the following formula (IV):

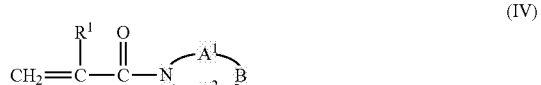

PRIOR ART DOCUMENTS

Patent Documents

Patent Document 1: Japanese unexamined Patent Application Publication (Translation of PCT Application) No. 2009-529562
Patent Document 2: Japanese unexamined Patent Application Publication (Translation of PCT Application) No. 2010-518190
Patent Document 3: Japanese Patent No. 2704730
Patent Document 4: Japanese Patent No. 4246022

SUMMARY OF THE INVENTION

Object to be Solved by the Invention

It is an object of the present invention to develop a novel acrylic copolymer suitable as a material for coating materials, ink, medicines for external use on skin, cosmetics and the like, and in particular, to develop a resin preferably used as a cosmetic, particularly, an out-bath type hair cosmetic. For example, it is the object of the present invention to develop a resin preferably used as a hair styling product capable of rearranging hair without flaking, thereby easily arranging hair style that realizes voluminousness and airly feeling, without fixing the hair strongly, a hair conditioner for dry hair, a hair styling product for thinning hair, etc.

Means to Solve the Object

As a result of intensive studies directed towards achieving the above-mentioned object, the present inventors have found that a silicone macromonomer is used to improve affinity for a silicone compound, a monomer having a quaternary ammonium salt is used to improve ability to adsorb on hair, and a (meth)acrylic monomer is used to adjust solubility and hardness, so that a resin particularly preferable for out-bath type hair cosmetics, etc. can be obtained, thereby completing the present invention.

Specifically, the present invention relates to the following (1) to (4):
(1) A (meth)acrylic silicone-based graft copolymer obtained by reacting the following radically polymerizable monomers (a), (b), (c) and (d), wherein the (meth)acrylic silicone-based graft copolymer is dissolved at a level of 50 mass % or more in 99.5% ethanol at 25° C.:
(a) a compound represented by the following general formula (I):

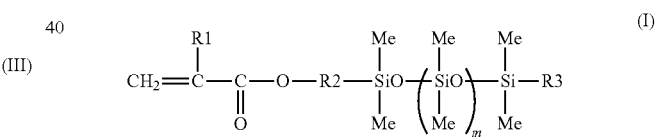

(wherein Me represents a methyl group, R1 represents a hydrogen atom or a methyl group, R2 represents a linear or branched divalent saturated hydrocarbon group containing 1 to 10 carbon atoms, which optionally comprises one or two ether bonds, R3 represents a saturated hydrocarbon group containing 1 to 10 carbon atoms, and m represents an integer of 5 to 100);
(b) at least one selected from
a compound represented by the following general formula (II):

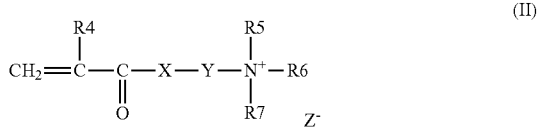

(wherein R4 represents a hydrogen atom or a methyl group, R5, R6 and R7, which are the same or different, each represent a hydrogen atom or an alkyl group containing 1 to 4 carbon atoms, X represents —O—, —NH—, —O—CH$_2$— or —O—CH$_2$CH(OH)—, Y represents a linear or branched divalent saturated hydrocarbon group containing 1 to 4 carbon atoms, and Z$^-$ represents a counter anion), and
a cationic compound represented by the following formula (III):

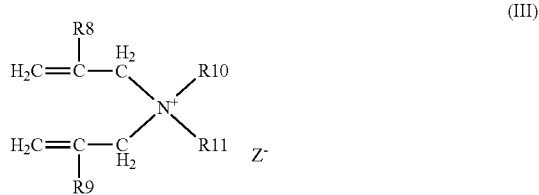

(wherein R8 and R9, which are the same or different, each represent a hydrogen atom or an alkyl group containing 1 to 4 carbon atoms, R10 and R11, which are the same or different, each represent a hydrogen atom or an alkyl group containing 1 to 18 carbon atoms, and Z$^-$ represents a counter anion);
(c) a compound represented by the following general formula (IV):

(wherein R12 represents a hydrogen atom or a methyl group, and R13 represents a hydrogen atom or a linear or branched alkyl group containing 1 to 3 carbon atoms); and
(d) a compound represented by the following general formula (V):

(wherein R14 represents a hydrogen atom or a methyl group, and R15 represents a hydroxyalkyl group containing 1 to 4 carbon atoms);
(2) The (meth)acrylic silicone-based graft copolymer according to (1) above, which further has a repeating unit derived from a (meth)acrylic derivative other than (a) to (d);
(3) The (meth)acrylic silicone-based graft copolymer according to (1) or (2) above, wherein with regard to the ratio of the monomers (a) to (d) used, (a)=20 to 50 mass %, (b)=0.5 to 4 mass %, (c) and (d)=46 to 79.5 mass %, and (c)/(d)=0.5 to 1.5; and
(4) The (meth)acrylic silicone-based graft copolymer according to any one of (1) to (3) above, wherein when the copolymer is dissolved at a level of 20 mass % in 99.5% ethanol, the viscosity of the ethanol solution at 25° C. is 50 to 250 mPa·s (CS).

In addition, the present invention relates to the following (5) and (6):
(5) A cosmetic comprising a (meth)acrylic silicone-based graft copolymer according to any one of (1) to (4) above; and
(6) The cosmetic according to (5) above, which is a hair cosmetic.

Effect of the Invention

Since the novel (meth)acrylic silicone-based graft copolymer of the present invention is soluble in ethanol and is also amphiphilic, it is useful as a material for cosmetics, coating materials, inks, medicines for external use on skin, etc.

Moreover, since the present (meth)acrylic silicone-based graft copolymer has high elasticity, when it is used particularly in out-bath type hair cosmetics, it is capable of easily arranging hair style that realizes voluminousness and airly feeling, by allowing hairs to softly adhere to one another, without fixing the hair strongly and without flaking. Furthermore, since the present (meth)acrylic silicone-based graft copolymer is also excellent in ability to adsorb on hair, it can impart smoothness as well as bounce and resilience to hair without stickiness, even if it is used in a small amount. Further, a resin is adsorbed on the cuticle of the damaged hair to reduce the unevenness on the surface of the hair, so that dry feeling can be reduced and the smoothness, flexibility, and bounce and resilience of healthy hair can be realized.

MODE OF CARRYING OUT THE INVENTION 1 (Meth)Acrylic Silicone-Based Graft Copolymer The (meth)acrylic silicone-based graft copolymer of the present invention is a polymer obtained by reacting at least the following radically polymerizable monomers (a), (b), (c) and (d). The present (meth)acrylic silicone-based graft copolymer also includes polymers obtained by reacting other copolymerizable monomers, in addition to the monomers (a) to (d).

The term "(meth)acryl" is used in the present invention to include acryl and methacryl.

The (meth)acrylic silicone-based graft copolymer of the present invention is dissolved at a level of 50 mass % or more in 99.5% ethanol at 25° C.

The ratio of individual monomers used is not particularly limited, as long as it provides the effect of the present invention. It is preferable that (a)=20 to 50 mass %, (b)=0.5 to 4 mass %, (c) and (d)=46 to 79.5 mass %, and (c)/(d)=0.5 to 1.5, based on the total mass of the monomers (a) to (d).

When copolymerizable monomers other than the monomers (a) to (d) are used, the monomers (a) to (d) are preferably used at a level of 66.5 mass % or more in total based on the total mass of the monomers.

It is to be noted that the term "ratio of monomers used" has roughly the same definitions as "the composition ratio of monomers in a copolymer."

The viscosity (unit: mPa·s=CS) of the (meth)acrylic silicone-based graft copolymer of the present invention that has been dissolved at a level of 20 mass % in 99.5% ethanol at 25° C., which is measured using a B type rotation viscometer, is 50 to 250, and preferably 70 to 150.

In addition, the Tg of the (meth)acrylic silicone-based graft copolymer of the present invention is preferably −10° C. to 40° C., and more preferably 0° C. to 30° C.

Herein, Tg indicates the Tg value calculated by the following Fox formula:

$$1/Tg = W_1/Tg_1 + W_2/Tg_2 + \ldots + W_n/Tg_n$$

In the above formula, $W_1$ to $W_n$ each indicate the mass fraction of each of an n type of monomers used in the synthesis of a base for hair cosmetics. $Tg_1$ to $Tg_n$ each represent the glass transition temperature of a homopolymer obtained by polymerization of each monomer alone.

Moreover, the (meth)acrylic silicone-based graft copolymer of the present invention includes various forms such as a random copolymer and a block copolymer.

Hereinafter, monomers used as raw materials for a copolymer will be described.

(a) Radically Polymerizable Monomer Represented by the Following General Formula (I)

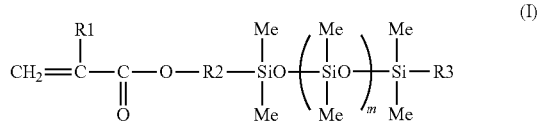

In the general formula (I), Me represents a methyl group, and R1 represents a hydrogen atom or a methyl group.

In addition, R2 represents a linear or branched divalent saturated hydrocarbon group containing 1 to 10 carbon atoms, which optionally comprises one or two ether bonds. Specific examples of such a linear or branched divalent saturated hydrocarbon group include —$CH_2$—, —$(CH_2)_2$—, —$(CH_2)_5$—, —$(CH_2)_{10}$—, —$CH_2$—$CH(CH_3)$—$CH_2$—, —$CH_2CH_2OCH_2CH_2CH_2$—, —$CH_2CH_2OCH_2(CH_3)CH_2$—, and —$CH_2CH_2OCH_2CH_2CH_2OCH_2CH_2$—.

R3 represents a saturated hydrocarbon group containing 1 to 10 carbon atoms. Specific examples of such a saturated hydrocarbon group include: alkyl groups containing 1 to 10 carbon atoms, such as a methyl group, an ethyl group, a n-propyl group, an i-propyl group, a n-butyl group, a s-butyl group, an i-butyl group, a t-butyl group, a n-pentyl group, a n-hexyl group, a n-nonyl group, an isononyl group, and a n-decyl group; cycloalkyl groups containing 3 to 10 carbon atoms, such as a cyclopropyl group, a cyclobutyl group, a cyclopentyl group, a cyclohexyl group, a cycloheptyl group, a cyclooctyl group, and a cyclododecyl group; and cycloalkylalkyl groups containing 4 to 10 carbon atoms, such as a cyclopropylmethyl group, a 2-cyclopropylethyl group, a cyclobutylmethyl group, a cyclopentylmethyl group, a 3-cyclopentylpropyl group, a cyclohexylmethyl group, a 2-cyclohexylethyl group, a cycloheptylmethyl group, and a cyclooctylmethyl group.

Also, in the formula, m represents an integer of 5 to 100.

The monomer represented by the formula (I) can be obtained, for example, by subjecting a (meth)acrylate-substituted chlorosilane compound represented by the following formula (1-a):

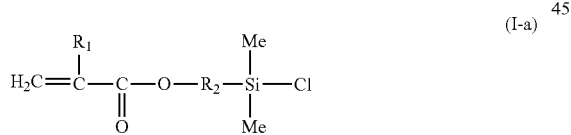

and polysiloxane comprising a substitution of a hydroxyl group at one end, represented by the following formula (1-b):

to a dehydrochlorination reaction according to an ordinary method. However, the synthetic method is not limited thereto.

Specific examples of the monomer represented by the formula (I) are as follows. It is to be noted that, in the following formulae, Me represents a methyl group and n-Bu represents a n-butyl group.

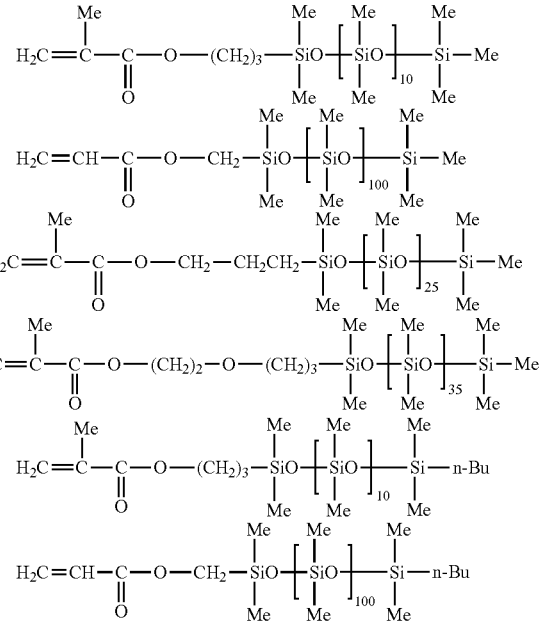

(b) Radically Polymerizable Monomer Represented by the Following Formula (II) or Formula (III)

Component (b) is at least one selected from cationic compounds represented by the following formula (II) and formula (III):

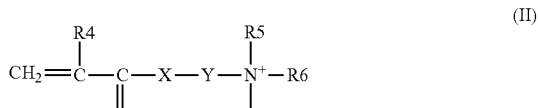

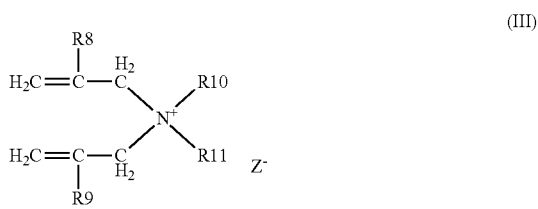

In the above formula (II), R4 represents a hydrogen atom or a methyl group.

R5, R6 and R7, which are the same or different, each represent a hydrogen atom or an alkyl group containing 1 to 4 carbon atoms. Examples of the alkyl group containing 1 to 4 carbon atoms include a methyl group, an ethyl group, a n-propyl group, an i-propyl group, a n-butyl group, a s-butyl group, an i-butyl group, and a t-butyl group.

X represents —O—, —NH—, —O—$CH_2$— or —O—$CH_2CH(OH)$—.

Y represents a linear or branched divalent saturated hydrocarbon group containing 1 to 4 carbon atoms. Examples of the linear or branched divalent saturated hydrocarbon group containing 1 to 4 carbon atoms include —$CH_2$—, —$(CH_2)_2$—, —$(CH_2)_3$—, —$(CH_2)_4$—, and —$CH_2$—$CH(CH_3)$—$CH_2$—.

$Z^-$ represents a counter anion. Examples of the counter anion include a chlorine ion, a bromine ion, a hydrogen sulfate ion, a nitric acid ion, a perchloric acid ion, a boron tetrafluoride ion, and a phosphorus hexafluoride ion.

In the above formula (III), R8 and R9, which are the same or different, each represent a hydrogen atom or an alkyl group containing 1 to 4 carbon atoms. Examples of the alkyl group containing 1 to 4 carbon atoms include a methyl group, an ethyl group, a n-propyl group, an i-propyl group, a n-butyl group, a s-butyl group, an i-butyl group, and a t-butyl group.

R10 and R11, which are the same or different, each represent a hydrogen atom or an alkyl group containing 1 to 18 carbon atoms. Examples of the alkyl group containing 1 to 18 carbon atoms include a methyl group, an ethyl group, a n-propyl group, an i-propyl group, a n-butyl group, a s-butyl group, an i-butyl group, a t-butyl group, a n-pentyl group, a n-hexyl group, a n-nonyl group, an isononyl group, a n-decyl group, a lauryl group, a tridecyl group, a myristyl group, a n-pentadecyl group, a palmityl group, a heptadecyl group, and a stearyl group.

(c) Radically Polymerizable Monomer Represented by the Following Formula (IV)

In the above formula, R12 represents a hydrogen atom or a methyl group.

R13 represents a hydrogen atom or a linear or branched alkyl group containing 1 to 3 carbon atoms. Examples of the linear or branched alkyl group containing 1 to 3 carbon atoms include a methyl group, an ethyl group, a n-propyl group, and an i-propyl group.

(d) Radically Polymerizable Monomer Represented by the Following Formula (V)

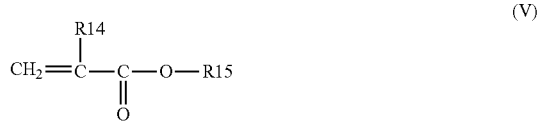

In the above formula, R14 represents a hydrogen atom or a methyl group.

R15 represents a hydroxyalkyl group containing 1 to 4 carbon atoms. Examples of the hydroxyalkyl group containing 1 to 4 carbon atoms include a hydroxymethyl group, a 2-hydroxyethyl group, a 3-hydroxy-n-propyl group, and a 4-hydroxy-n-butyl group.

(e) Other Copolymerizable Monomers

Other copolymerizable monomers include the following compounds.

((Meth)acrylic monomers)

n-Butyl(meth)acrylate, isobutyl(meth)acrylate, t-butyl (meth)acrylate, 2-ethylhexyl(meth)acrylate, n-hexyl(meth) acrylate, n-octyl(meth)acrylate, cyclohexyl(meth)acrylate, decyl(meth)acrylate, undecyl(meth)acrylate, lauryl(meth) acrylate, tridecyl(meth)acrylate, myristyl(meth)acrylate, pentadecyl(meth)acrylate, palmityl(meth)acrylate, heptadecyl(meth)acrylate, stearyl(meth)acrylate, isostearyl(meth) acrylate, oleyl(meth)acrylate, behenyl(meth)acrylate, and (meth)acrylic ester having a linear, branched or alicyclic hydrocarbon group; acrylonitrile; (meth)acrylamides such as acrylamide, diacetone acrylamide, N,N-dimethylacrylamide, N-t-butylacrylamide, N-octylacrylamide and N-t-octylacrylamide; (meth)acrylamides containing a sulfonic acid group, such as 2-(meth)acrylamide-2-methylpropanesulfonic acid; alkylaminoalkyl(meth)acrylates such as aminoethyl(meth) acrylate, t-butylaminoethyl methacrylate and methylaminoethyl(meth)acrylate; dialkylaminoalkyl(meth)acrylates such as dimethylaminoethyl(meth)acrylate and diethylaminoethyl (meth)acrylate; dialkylaminoalkyl(meth)acrylamides such as dimethylaminoethyl(meth)acrylamide and diethylaminoethyl(meth)acrylamide; esters from cyclic compounds and (meth)acrylic acids, such as tetrahydrofurfuryl(meth)acrylate, isobornyl(meth)acrylate and glycidyl(meth)acrylate; (meth)acrylic acid alkoxy alkyl esters such as ethoxyethyl (meth)acrylate and methoxyethyl(meth)acrylate; monoesters from polyalkylene glycols and (meth)acrylic acids, such as polyethylene glycol mono(meth)acrylate and polypropylene glycol mono(meth)acrylate; (meth)acryl esters containing a sulfonic acid group; methacryloyloxy alkyl phosphate monoesters such as (meth)acryloyloxy ethyl phosphate; glyceryl(meth)acrylate, 2-methacryloyloxyethylsuccinic acid, 2-(meth)acryloyloxyethylphthalic acid, β-carboxyethyl acrylate, acryloyloxyethyl succinate, 2-(meth)acryloyloxyethyltetrahydrophthalic acid and 2-(meth)acryloyloxyethylhexahydrophthalic acid; and (meth)acrylates having two or more ethylenically unsaturated double bonds, such as 1,4-butanediol di(meth)acrylate, 1,6-hexanediol di(meth)acrylate, ethylene glycol di(meth)acrylate, polyethylene (n=2 to 50) glycol di(meth)acrylate, propylene glycol di(meth)acrylate, polypropylene (n=2 to 50) glycol di(meth)acrylate, butylene glycol di(meth)acrylate, dipentyl glycol di(meth)acrylate, neopentyl glycol di(meth)acrylate, trimethylolpropane di(meth)acrylate, methylene bisacrylamide, bisphenol F EO-modified (n=2 to 50) di(meth)acrylate, bisphenol A EO-modified (n=2 to 50) diacrylate, bisphenol S EO-modified (n=2 to 50) di(meth)acrylate, trimethylolethane tri(meth) acrylate, trimethylolpropane tri(meth)acrylate, trimethylolpropane tricaprolactonate tri(meth)acrylate, trimethylolhexane tri(meth)acrylate, pentaerythritol tri (meth)acrylate, pentaerythritol tetra(meth)acrylate, diglycerine tetra(meth)acrylate, ditrimethylolpropane tetra(meth) acrylate, ditrimethylolpropane tetracaprolactonate, tetra (meth)acrylate, ditrimethylolethane tetra(meth)acrylate, ditrimethylolbutane tetra(meth)acrylate, ditrimethylolhexane tetra(meth)acrylate, dipentaerythritol penta(meth)acrylate, dipentaerythritol hexa(meth)acrylate, tripentaerythritol hexa(meth)acrylate, tripentaerythritol hepta(meth)acrylate and tripentaerythritol octa(meth)acrylate.

(Monomers Other than (Meth)Acrylic Monomers)

Unsaturated monocarboxylic acids such as crotonic acid; aromatic vinyl compounds such as styrene; unsaturated dicarboxylic acids such as itaconic acid, maleic acid, fumaric acid, maleic anhydride and citraconic acid; monoalkyl esters of unsaturated dicarboxylic acids, such as maleic acid monoalkyl ester, fumaric acid monoalkyl ester and itaconic acid monoalkyl ester; monomers containing a sulfonic acid group, for example, alkene sulfonic acids such as vinylsulfonic acid and (meth)allylsulfonic acid; aromatic vinyl group-containing sulfonic acids such as α-methylstyrenesulfonic acid; primary to tertiary amino group-containing unsaturated compounds such as (meth)allylamine; amino group-containing aromatic vinyl compounds such as N,N-dimethylaminostyrene; compounds having two or more ethylenically unsaturated double bonds, such as divinylbenzene, diisopropenylbenzene and trivinylbenzene; urethane oligomers having two or more ethylenically unsaturated double bonds; silicone compounds having two or more ethylenically unsaturated double bonds; and vinyl acetate and vinyl pyrrolidone.

2 Production Method

In the present invention, copolymerization of the above described radically polymerizable monomers (a) to (d) and other copolymerizable (meth)acrylic monomers used as necessary is not particularly limited. These monomers can be copolymerized by a known method. For instance, copolymerization can be carried out in the presence of a common radical polymerization initiator such as benzoyl peroxide, lauroyl peroxide or azobisisobutyronitrile. Any method of a solution polymerization method, an emulsification polymerization method, a suspension polymerization method, and a bulk polymerization method can be applied herein. Among these methods, the solution polymerization method is preferable because it can easily adjust the molecular weight of the obtained graft copolymer to the optimal range. Examples of a solvent used herein include: aromatic hydrocarbons such as benzene, toluene or xylene; ketones such as methyl ethyl ketone or methyl isobutyl ketone; esters such as ethyl acetate or isobutyl acetate; and alcohols such as isopropanol or butanol. The solvent may be used singly or in the form of a mixture consisting of two or more types as described above.

The polymerization reaction can be carried out in a temperature range from 50° C. to 180° C., and preferably from 60° C. to 120° C. The reaction can be terminated for approximately 5 to 10 hours under the above-mentioned conditions.

3 Intended Use

The (meth)acrylic silicone-based graft copolymer of the present invention can be used singly or in combination of two or more types, for various intended uses such as medicines for external use on skin, additives for coating materials or ink, materials for sanitary goods, additives for papers, sizing agents, or food additives, as well as cosmetics. The present (meth)acrylic silicone-based graft copolymer is preferably used for cosmetics, and in particular, it is more preferably mixed into out-bath type cosmetics. Examples of such cosmetics include: hair cosmetics; skin care cosmetics such as skin lotion, emulsion, cream, beauty essence, and facial mask; make up cosmetics such as eye shadow, powder foundation, liquid foundation, concealer, face powder, mascara, lipstick, eyebrow, eyeliner, and manicure; and sunscreen. Among others, out-bath type hair cosmetics are preferable.

The mixing ratio of the (meth)acrylic silicone-based graft copolymer of the present invention can be determined, as appropriate, depending on intended use. The present (meth) acrylic silicone-based graft copolymer is mixed into a cosmetic in an amount of generally 0.01 to 10 mass %, and preferably 0.02 to 5 mass %, based on the total mass of the cosmetic.

In general, components used for cosmetics or pharmaceutical agents such as quasi drugs or medicines for external use, namely, water (purified water, hot spring water, deep water, etc.), oil agents, surfactants, metallic soaps, gelling agents, powders, alcohols, water-soluble polymers, film-forming agents, resins, inclusion compounds, moisturizers, antimicrobial agent, fragrances, deodorants, salts, pH adjusters, refrigerants, plant extracts, vitamins, amino acids, peptides, other beauty components for hair care, and the like, can be mixed into a cosmetic containing the (meth)acrylic silicone-based graft copolymer of the present invention, within a range which does not impair the effect of the present invention.

Examples of the oil agent that can be used herein include oily components such as a volatile oil agent, higher alcohol, hydrocarbon oil, ester oil, fatty acids, oils and fats, and silicone.

Specific Examples Include:

volatile oil agents such as light isoparaffin, cyclic silicone, and volatile dimethylpolysiloxane;

higher alcohols such as lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, sitosterol, lanosterol, and monostearyl glycerin ether (batyl alcohol);

hydrocarbons such as ozokerite, squalane, squalene, ceresin, paraffin, paraffin wax, liquid paraffin, pristane, polyisobutylene, microcrystalline wax, and Vaseline;

ester oils such as diisobutyl adipate, 2-hexyldecyl adipate, di-2-heptylundecyl adipate, monoisostearic acid-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, isopropyl myristate, octyldodecyl myristate, 2-hexyldecyl myristate, myristyl myristate, hexyldecyl dimethyloctanoate, ethyl laurate, hexyl laurate, and diisostearyl malate;

waxes such as beeswax, carnauba wax, candelilla wax, and spermaceti;

animal oils such as tallow, neat's foot oil, beef bone fat, hardened tallow, hardened oil, turtle oil, lard, horse fat, mink oil, cod liver oil, and egg-yolk oil;

lanolin derivatives such as lanolin, liquid lanolin, reduced lanolin, lanolin alcohol, hard lanolin, lanolin acetate, and lanolin fatty acid isopropyl;

fatty acids such as lauric acid, myristic acid, palmitic acid, stearic acid, behenic acid, undecylenic acid, oleic acid, linolic acid, arachidonic acid, docosahexaenoic acid (DHA), isostearic acid, and 12-hydroxystearic acid; and low polymerized dimethylpolysiloxane, high polymerized dimethylpolysiloxane, methylphenyl polysiloxane, decamethylcyclopentasiloxane, octamethylcyclotetrasiloxane, polyether-modified polysiloxane, polyoxyalkylene/alkylmethylpolysiloxane/methylpolysiloxane copolymer, alkoxy-modified polysiloxane, alkyl-modified polysiloxane, crosslinked organopolysiloxane, fluorine-modified polysiloxane, amino-modified polysiloxane, glycerin-modified polysiloxane, higher alkoxy-modified silicone, higher fatty acid-modified silicone, silicone resin, silicone rubber, and silicone resin.

The surfactant may be any one of cationic, nonionic, and anionic surfactants.

Examples of the cationic surfactant include: quaternary ammonium salts such as cetyl trimethyl ammonium chloride, cetyl trimethyl ammonium bromide, stearyl trimethyl ammonium chloride, stearyl trimethyl ammonium bromide, behenyl trimethyl ammonium chloride, behenyl trimethyl ammonium bromide, behenyl trimethyl ammonium methylsulfate, distearyl dimethyl ammonium chloride, dioleyl dimethyl ammonium bromide, cetyl behenyl dimethyl ammonium methylsulfate, and stearyl dimethyl benzyl ammonium chloride; mono-N-long chain acyl basic amino acid lower alkyl ester salts such as stearoyl lysine butyl ester hydrochloride, N-coconut oil fatty acid acyl L-arginine ethyl DL-pyrrolidone carboxylate, and lauroyl-ornithine propyl ester acetate; and guanidine derivatives such as decyl guanidine acetate, 2-guanidino ethyl lauryl amide hydrochloride, and 2-guanidino butyl stearamide DL-pyrrolidone carboxylate. In the present invention, quaternary ammonium salts such as cetyl trimethyl ammonium chloride, cetyl trimethyl ammonium bromide, stearyl trimethyl ammonium chloride, stearyl trimethyl ammonium bromide, behenyl trimethyl ammonium chloride, behenyl trimethyl ammonium bromide, and distearyl dimethyl ammonium chloride are particularly preferable. For example, commercially available products such as "GENAMINE STAC" (manufactured by Clariant Japan K. K.) and "GENAMINE KDM-P" (manufactured by Clariant Japan K. K.) can be used as cationic surfactants in the present invention.

Examples of the nonionic surfactant include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene alkyl ether, polyoxypropylene alkyl ether, polyoxyethylene alkyl phenyl ether, polyoxyethylene fatty acid ester, polyoxyethylene sorbitan fatty acid ester, polyoxyethylene sorbitol fatty acid ester, polyoxyethylene glycerin fatty acid ester, polyoxyethylene propylene glycol fatty acid ester, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopolysiloxane, polyoxyalkylene/alkyl co-modified organopolysiloxane, diethanolamide laurate, coconut oil fatty acid diethanolamide, coconut oil fatty acid monoethanolamide, polyoxyethylene coconut oil fatty acid monoethanolamide, monoisopropanolamide laurate, coconut oil fatty acid mono isopropanolamide, polyoxypropylene coconut oil fatty acid monoisopanolamide, alkanolamide, sugar ether, and sugar amide.

Examples of the anionic surfactant include: higher fatty acid salts such as sodium laurate, potassium laurate, and potassium coconut oil fatty acid; polyoxyethylene alkyl ether sulfates such as sodium polyoxyethylene lauryl ether sulfate, ammonium polyoxyethylene lauryl ether sulfate, and triethanolamine polyoxyethylene lauryl ether sulfate; alkyl sulfates such as sodium lauryl sulfate and triethanolamine lauryl sulfate; α-olefin sulfonates such as sodium tetradecene sulfonate and potassium tetradecene sulfonate; hydroxy ether carboxylates such as dodecane-1,2-diol acetate ether sodium; and sulfosuccinic acids such as sodium sulfosuccinate.

Examples of the metallic soap include aluminum isostearate, zinc stearate, aluminum stearate, calcium stearate, magnesium stearate, zinc myristate, magnesium myristate, zinc cetyl phosphate, calcium cetyl phosphate, sodium zinc cetyl phosphate, zinc laurate, and zinc undecylenate.

Examples of the gelling agent include: amino acid derivatives such as α,γ-di-n-butylamine; dextrin fatty acid esters such as dextrin palmitic acid ester, dextrin stearic acid ester, and dextrin 2-ethylhexanoic acid palmitic acid ester; sucrose fatty acid esters such as sucrose palmitic acid ester, and sucrose stearic acid ester; benzylidene derivatives of sorbitol, such as monobenzylidene sorbitol and dibenzylidene sorbitol; and organic-modified clay minerals such as dimethylbenzyldodecyl ammonium montmorillonite clay and dimethyldioctadecyl ammonium montmorillonite clay.

The shape (spherical, acicular, platy, etc.), particle diameter (fumy, fine particle, pigment, etc.), and particle structure (porous, nonporous, etc.) of powders are not limited, as long as the powders may be used for common cosmetics. All types of powders can be used herein. Examples of the powders used herein include: inorganic powders such as magnesium oxide, barium sulfate, calcium sulfate, magnesium sulfate, calcium carbonate, magnesium carbonate, talc, synthetic mica, mica, kaoline, sericite, muscovite, phlogopite, lepidolite, biotite, lithia mica, silicic acid, silicic acid anhydride, aluminum silicate, magnesium silicate, aluminum magnesium silinate, calcium silicate, barium silicate, strontium silicate, tungsten metal salt, hydroxyapatite, vermiculite, HIGILITE, montmorillonite, zeolite, ceramics powder, calcium secondary phosphate, alumina, aluminum hydroxide, and boron nitride; organic powders such as polyamide powder, polyester powder, polyethylene powder, polypropylene powder, polystyrene powder, polyurethane, benzoguanamine powder, polymethylbenzoguanamine powder, tetrafluoroethylene powder, polymethyl methacrylate powder, cellulose, silk powder, nylon powder, nylon 12, nylon 6, styrene/acrylic acid copolymer, divinylbenzene/styrene copolymer, vinyl resin, urea resin, phenol resin, fluorocarbon resin, silicon resin, acrylic resin, melamine resin, epoxy resin, polycarbonate resin, microcrystalline fiber powder, and lauroyl lysine; colored pigments including inorganic red pigments such as iron oxide, iron hydroxide and iron titanate, inorganic brown pigments such as γ-iron oxide, inorganic yellow pigments such as yellow iron oxide and loess, inorganic black pigments such as black iron oxide and carbon black, inorganic violet pigments such as manganese violet and cobalt violet, inorganic green pigments such as chromium hydroxide, chromium oxide, cobalt oxide and cobalt titanate, inorganic blue pigments such as iron blue and ultramarine blue, laked tar pigments, laked natural pigments, and composite powder formed by conjugation of these powders; pearl pigments such as titanium oxide-coated mica, titanium oxide-coated mica, bismuth oxychloride, titanium oxide-coated bismuth oxychloride, titanium oxide-coated talc, argentine, and titanium oxide-coated colored isinglass; metallic powder pigments such as aluminum powder, copper powder, and stainless steel powder; tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; natural pigments that are powders selected from carmic acid, laccaic acid, carthamin, brazilin and crocin, wherein these powders may be conjugated with one another, or the surface of which may be treated with an oil agent, silicone, or a fluorine compound.

Examples of the alcohols include: lower alcohols such as ethanol and isopropanol; and polyhydric alcohols such as glycerin, diglycerin, ethylene glycol, diethylene glycol, triethylene glycol, propylene glycol, dipropylene glycol, 1,3-butylene glycol, and polyethylene glycol.

Examples of the water-soluble polymer include: mucopolysaccharide selected from chondroitin sulfuric acid, hyaluronic acid, mucin, dermatan sulfate, heparin, and keratan sulfate and a salt thereof; plant-based polymers such as gum Arabic, Tragacanth, galactan, carob gum, guar gum, karaya gum, carrageenan, pectin, agar, quince seed, algal colloids, traganth gum, locust bean gum, and galactomannan; microorganism-based polymers such as xanthan gum, dextran, succinoglucan, and pullulan; starch-based polymers such as starch, carboxymethyl starch and methylhydroxypropyl starch; cellulose-based polymers such as methyl cellulose, methylhydroxypropyl cellulose, carboxymethyl cellulose, hydroxymethyl cellulose, hydroxypropyl cellulose, cellulose sodium sulfate, carboxymethyl cellulose sodium, crystalline cellulose, and cellulose powder; alginic acid-based polymers such as sodium alginate and alginic acid propylene glycol ester; vinyl-based polymers such as a carboxy vinyl polymer and an alkyl-modified carboxy vinyl polymer; acrylic polymers such as a polyoxyethylene polymer, a polyoxyethylene polyoxypropylene copolymer polymer, sodium polyacrylate, and polyacrylamide; and inorganic water-soluble polymers such as polyethyleneimine, bentonite, laponite, and hectorite. In addition, these polymers also include film-forming agents such as polyvinyl alcohol and polyvinyl pyrrolidone.

Examples of the antimicrobial agent include benzoic acid, sodium benzoate, salicylic acid, carbolic acid, sorbic acid, potassium sorbate, p-oxybenzoic acid ester, p-chlorometacresol, hexachlorophene, benzalkonium chloride, chlorhexidine chloride, trichlorocarbanilide, photosensitizing dye, bis (2-pyridylthio-1-oxide) zinc, phenoxy ethanol, and isopropylmethyl phenol.

Examples of the pH adjuster include lactic acid, citric acid, glycolic acid, succinic acid, tartaric acid, malic acid, potassium carbonate, sodium bicarbonate, ammonium bicarbonate, sodium hydroxide, potassium hydroxide, triethanolamine, and monoethanolamine. Examples of the refrigerant include l-menthol and camphor.

Examples of the vitamins include: vitamin A and a derivative thereof; vitamin B and a derivative thereof; vitamin C and a derivative thereof; vitamin E and a derivative thereof; vitamins F such as linolenic acid and a derivative thereof; vitamins K such as phytonadione, menaquinone, menadione, and menadiol; vitamins P such as eriocitrin and hesperidin; and others such as biotin, carnitine, and ferulic acid.

Examples of the amino acids include glycine, alanine, valine, isoleucine, serine, threonine, aspartic acid, glutamic acid, asparagine, glutamine, lysine, hydroxylysine, arginine, cystine, cysteine, acetyl cysteine, methionine, phenylalanine, tyrosine, proline, hydroxyproline, ornithine, citrulline, theanine, creatine, and creatinine. Examples of amino acid derivatives include di(phytosteryl/2-octyldodecyl) N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/2-octyldodecyl) N-lauroyl-L-glutamate, di(2-octyldodecyl) N-lauroyl-L-glutamate, and an N-acyl glutamic acid lysine condensation product.

The peptides may be derived from any of animals, fish, shell and plants. Specific examples of such peptides include collagen and a derivative thereof or a hydrolysate thereof, elastin and a derivative thereof or a hydrolysate thereof, keratin and a derivative thereof or a hydrolysate thereof, a wheat protein and a derivative thereof or a hydrolysate thereof, and a soybean protein and a derivative thereof or a hydrolysate thereof.

Examples of the sugars include sorbitol, erythritol, maltose, maltitol, xylitol, xylose, trehalose, inositol, glucose, mannitol, pentaerythritol, fructose, sucrose and an ester thereof, dextrin and a derivative thereof, honey, and a brown sugar extract.

Other components used herein include: hair lipid components such as ceramide and a derivative thereof, and 18-methyl eicosanoic acid; phosphatidyl choline, phosphatidylethanolamine, phosphatidyl serine, phosphatidyl glycerol, phosphatidyl inositol, sphingophospholipid, analogs thereof, compositions containing these components, such as soybean lecithin and egg yolk lecithin, and hydrogenated products thereof; phospholipids and derivatives thereof, such as a single polymer of 2-methacryloyloxyethylphosphorylcholine, a copolymer of 2-methacryloyloxyethylphosphorylcholine and a hydrophobic monomer; and beauty components useful for hair care, such as moisture retention or repair of hair.

One or more types may be selected, as appropriate, from the above-listed components and may be then used, or these components may be used in combination.

The cosmetic of the present invention may have any dosage form of aqueous, water-soluble, O/W type emulsion, W/O type emulsion, oily, and solid powdery forms. In addition, the present cosmetic may also have any dosage form of liquid, emulsion, cream, gel, solid forms. Moreover, it is also possible that a propellant be mixed into the present cosmetic and that the obtained mixture be then added into an aerosol foam or pump foam container, so that the present cosmetic can be used as a foam-type product. The present cosmetic is particularly preferably used as an out-bath type hair cosmetic such as styling spray, styling mousse, hair mist, hair wax, hair cream or hair essence.

EXAMPLES

Hereinafter, the present invention will be described in the following examples. However, these examples are not intended to limit the technical scope of the present invention. In addition, the symbol "%" is used to mean "mass %" in the examples.

1 Production of (Meth)Acrylic Silicone-Based Graft Copolymer

Production Example 1

4 g of dimethyl 2,2-azobis(2-methyl propionate) (V-601)[Note 2], 40 g of one end methacrylate-substituted dimethylpolysiloxane (X-24-8201)[Note 3], 31 g of ethyl acrylate (EA)[Note 4], 27 g of 2-hydroxyethyl methacrylate (HEMA)[Note 5], 4 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 87 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

The ratio of the added monomers is as follows.
MAPTAC:EA:HEMA:X-24-8201=2:31:27:40
(Note 1) IPA, manufactured by Kanto Chemical Co., Inc.
(Note 2) V-601, manufactured by Wako Pure Chemical Industries, Ltd.
(Note 3) X-24-8201, manufactured by Shin-Etsu Chemical Co., Ltd.
(Note 4) EA, manufactured by Kanto Chemical Co., Inc.
(Note 5) HEMA, manufactured by Kanto Chemical Co., Inc.

(Note 6) MAPTAC, manufactured by Evonik Degussa Japan Co., Ltd., 50% aqueous solution Production Example 2

4 g of dimethyl 2,2-azobis(2-methyl propionate)[Note 2], 40 g of one end methacrylate-substituted dimethylpolysiloxane (X-22-174DX)[Note 7], 31 g of ethyl acrylate[Note 4], 27 g of 2-hydroxyethyl methacrylate[Note 5], 4 g of 3-trimethylammonium propyl methacrylamide chloride[Note 6], and 170 g of isopropanol[Note 1] were added to 50 g of isopropanol[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 90 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-22-174DX=2:31:27:40

(Note 7) X-22-174DX, manufactured by Shin-Etsu Chemical Co., Ltd.

Production Example 3

4 g of dimethyl 2,2-azobis(2-methyl propionate)[Note 2], 40 g of one end methacrylate-substituted dimethylpolysiloxane (X-22-174ASX)[Note 8], 31 g of ethyl acrylate[Note 4], 27 g of 2-hydroxyethyl methacrylate[Note 5], 4 g of 3-trimethylammonium propyl methacrylamide chloride[Note 6], and 50 g of isopropanol[Note 1] were added to 100 g of isopropanol[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 83 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-22-174ASX=2:31:27:40

(Note 8) X-22-174ASX, manufactured by Shin-Etsu Chemical Co., Ltd.

Production Example 4

4 g of dimethyl 2,2-azobis(2-methyl propionate)[Note 2], 40.4 g of one end methacrylate-substituted dimethylpolysiloxane (X-24-8201)[Note 3], 27.3 g of ethyl acrylate[Note 4], 31.3 g of 2-hydroxyethyl methacrylate[Note 5], 2 g of 3-trimethylammonium propyl methacrylamide chloride[Note 6], and 50 g of isopropanol[Note 1] were added to 100 g of isopropanol[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 86 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-24-8201=1:27.3:31.3:40.4

Production Example 5

4 g of dimethyl 2,2-azobis(2-methyl propionate)[Note 2], 40 g of one end methacrylate-substituted dimethylpolysiloxane (X-24-8201)[Note 3], 26 g of ethyl acrylate[Note 4], 30 g of 2-hydroxyethyl methacrylate[Note 5], 8 g of 3-trimethylammonium propyl methacrylamide chloride[Note 6], and 120 g of isopropanol[Note 1] were added to 50 g of isopropanol[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 83 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-24-8201=4:26:30:40

Production Example 6

4 g of dimethyl 2,2-azobis(2-methyl propionate)[Note 2], 20 g of one end methacrylate-substituted dimethylpolysiloxane (X-24-8201)[Note 3], 41.5 g of ethyl acrylate[Note 4], 36.5 g of 2-hydroxyethyl methacrylate[Note 5], 4 g of 3-trimethylammonium propyl methacrylamide chloride[Note 6], and 50 g of isopropanol[Note 1] were added to 100 g of isopropanol[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 86 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-24-8201=2:41.5:36.5:20

Production Example 7

4 g of dimethyl 2,2-azobis(2-methyl propionate)[Note 2], 50 g of one end methacrylate-substituted dimethylpolysiloxane (X-24-8201)(Note 3), 23 g of ethyl acrylate(Note 4), 25 g of 2-hydroxyethyl methacrylate(Note 5), 4 g of 3-trimethylammonium propyl methacrylamide chloride(Note 6), and 100 g of isopropanol(Note 1) were added to 50 g of isopropanol(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in IPA was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 96 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-24-8201=2:23:25:50

Production Example 8

4 g of dimethyl 2,2-azobis(2-methyl propionate) (V-601)(Note 2), 40 g of one end methacrylate-substituted dimethylpolysiloxane (X-24-8201)(Note 3), 31 g of ethyl acrylate (EA)(Note 4), 27 g of 2-hydroxyethyl methacrylate (HEMA)(Note 5), 3.34 g of dimethyldiallylammonium chloride (DADMAC)(Note 9), and 50 g of isopropanol(Note 1) were added to 100 g of isopropanol (IPA)(Note 1), while stirring, in a three-necked flask in a nitrogen atmosphere at 70° C. to 80° C. for 3 to 4 hours. Subsequently, 1 g of dimethyl 2,2-azobis (2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 87 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

The ratio of the added monomers is as follows.
DADMAC:EA:HEMA:X-24-8201=2:31:27:40
(Note 9) DADMAC, manufactured by Tokyo Chemical Industry Co., Ltd., 60% aqueous solution Production Example 9

4 g of dimethyl 2,2-azobis(2-methyl propionate) (V-601)(Note 2), 40 g of one end methacrylate-substituted dimethylpolysiloxane (X-24-8201)(Note 3), 30 g of ethyl acrylate (EA)(Note 4), 27 g of 2-hydroxyethyl methacrylate (HEMA)(Note 5), 6 g of 3-trimethylammonium propyl methacrylamide chloride (MAPTAC)(Note 6), and 50 g of isopropanol(Note 1) were added to 100 g of isopropanol (IPA)(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 89 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 11° C.

The ratio of the added monomers is as follows.
MAPTAC:EA:HEMA:X-24-8201=3:30:27:40

Production Example 10

4 g of dimethyl 2,2-azobis(2-methyl propionate) (V-601)(Note 2), 30 g of one end methacrylate-substituted dimethylpolysiloxane (X-24-8201)(Note 3), 35 g of ethyl acrylate (EA)(Note 4), 32 g of 2-hydroxyethyl methacrylate (HEMA)(Note 5), 6 g of 3-trimethylammonium propyl methacrylamide chloride (MAPTAC)(Note 6), and 50 g of isopropanol(Note 1) were added to 100 g of isopropanol (IPA)(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 88 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 11° C.

The ratio of the added monomers is as follows.
MAPTAC:EA:HEMA:X-24-8201=3:35:32:30

Production Example 11

4 g of dimethyl 2,2-azobis(2-methyl propionate) (V-601)(Note 2), 30 g of one end methacrylate-substituted dimethylpolysiloxane (X-24-8201)(Note 3), 36 g of ethyl acrylate (EA)(Note 4), 32 g of 2-hydroxyethyl methacrylate (HEMA)(Note 5), 4 g of 3-trimethylammonium propyl methacrylamide chloride (MAPTAC)(Note 6), and 50 g of isopropanol(Note 1) were added to 100 g of isopropanol (IPA)(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 88 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 11° C.

The ratio of the added monomers is as follows.
MAPTAC:EA:HEMA:X-24-8201=2:36:32:30

Production Example 12

4 g of dimethyl 2,2-azobis(2-methyl propionate) (V-601)[Note 2], 30 g of one end methacrylate-substituted dimethylpolysiloxane (X-24-8201)[Note 3], 37 g of ethyl acrylate (EA)[Note 4], 32 g of 2-hydroxyethyl methacrylate (HEMA)[Note 5], 2 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 90 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 10° C.

The ratio of the added monomers is as follows.
MAPTAC:EA:HEMA:X-24-8201=1:37:32:30

Production Example 13

4 g of dimethyl 2,2-azobis(2-methyl propionate) (V-601)[Note 2], 30 g of one end methacrylate-substituted dimethylpolysiloxane (X-22-174DX)[Note 7], 36 g of ethyl acrylate (EA)[Note 4], 32 g of 2-hydroxyethyl methacrylate (HEMA)[Note 5], 4 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 86 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 11° C.

The ratio of the added monomers is as follows.
MAPTAC:EA:HEMA:X-22-174DX=2:36:32:30

Production Example 14

4 g of dimethyl 2,2-azobis(2-methyl propionate) (V-601)[Note 2], 40 g of one end methacrylate-substituted dimethylpolysiloxane (X-24-8201)[Note 3], 16 g of ethyl acrylate (EA)[Note 4], 42 g of 2-hydroxyethyl methacrylate (HEMA)[Note 5], 2 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 91 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 30° C.

The ratio of the added monomers is as follows.
MAPTAC:EA:HEMA:X-24-8201=1:16.2:42.4:40.4

Production Example 15

4 g of dimethyl 2,2-azobis(2-methyl propionate) (V-601)[Note 2], 40 g of one end methacrylate-substituted dimethylpolysiloxane (X-24-8201)[Note 3], 27 g of ethyl acrylate (EA)[Note 4], 31 g of 2-hydroxyethyl methacrylate (HEMA)[Note 5], 2 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 88 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 15° C.

The ratio of the added monomers is as follows.
MAPTAC:EA:HEMA:X-24-8201=1:27.3:31.3:40.4

Production Example 16

4 g of dimethyl 2,2-azobis(2-methyl propionate) (V-601)(Note 2), 20.2 g of one end methacrylate-substituted dimethylpolysiloxane (X-24-8201)(Note 3), 65.7 g of ethyl acrylate (EA)(Note 4), 13.1 g of 2-hydroxyethyl methacrylate (HEMA)(Note 5), 2 g of 3-trimethylammonium propyl methacrylamide chloride (MAPTAC)(Note 6), and 50 g of isopropanol(Note 1) were added to 100 g of isopropanol (IPA)(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 87 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is −10° C.

The ratio of the added monomers is as follows.
MAPTAC:EA:HEMA:X-24-8201=1:65.7:13.1:20.2

Comparative Production Example 1

Example of 0% MAPTAC 4 g of dimethyl 2,2-azobis(2-methyl propionate)(Note 2), 40 g of one end methacrylate-substituted dimethylpolysiloxane (X-24-8201)(Note 3), 33 g of ethyl acrylate(Note 4), 27 g of 2-hydroxyethyl methacrylate(Note 5), and 100 g of isopropanol(Note 1) were added to 50 g of isopropanol(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 89 g of a transparent rubber-like product.

It was confirmed by infrared absorption spectrometry that the obtained rubber-like product was a desired (meth)acrylic silicone-based graft copolymer.

The ratio of the added monomers is as follows.
EA:HEMA:X-24-8201=33:27:40

Comparative Production Example 2

Example of 0% X-24-8201

4 g of dimethyl 2,2-azobis(2-methyl propionate)(Note 2), 51 g of ethyl acrylate(Note 4), 47 g of 2-hydroxyethyl methacrylate(Note 5), 4 g of 3-trimethylammonium propyl methacrylamide chloride(Note 6), and 40 g of isopropanol(Note 1) were added to 100 g of isopropanol(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in IPA was added to the resulting solution, and the obtained mixture was then reacted in a temperature range from 70° C. to 80° C. for 5 hours, so as to obtain a viscous solution. This solution was poured into hexane, so that a graft polymer was deposited and precipitated. Thereafter, the precipitate was separated by filtration, and was then dried at 80° C. under a reduced pressure, so as to obtain 89 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA=2:51:47

Comparative Production Example 3

Example of 0% EA 4 g of dimethyl 2,2-azobis(2-methyl propionate)(Note 2), 50 g of one end methacrylate-substituted dimethylpolysiloxane (X-24-8201)(Note 3), 25 g of 2-hydroxyethyl methacrylate(Note 5), 4 g of 3-trimethylammonium propyl methacrylamide chloride(Note 6), and 100 g of isopropanol(Note 1) were added to 50 g of isopropanol(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into hexane, so that a graft polymer was deposited and precipitated. Thereafter, the precipitate was separated by filtration, and was then dried at 80° C. under a reduced pressure, so as to obtain 95 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:HEMA:X-24-8201=2:58:40

Comparative Production Example 4

Example of 0% HEMA 4 g of dimethyl 2,2-azobis(2-methyl propionate)(Note 2), 40 g of one end methacrylate-substituted dimethylpolysiloxane (X-24-8201)(Note 3), 58 g of ethyl acrylate(Note 4), 4 g of 3-trimethylammonium propyl methacrylamide chloride(Note 6), and 100 g of isopropanol(Note 1) were added to 50 g of isopropanol(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 93 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:X-24-8201=2:58:40

2 Evaluation of (Meth)Acrylic Silicone-Based Graft Copolymer

(1) Properties of Coating Film

A 20% ethanol solution, in which the copolymers obtained in the above described Production Example 2, Production Examples 9 to 16 and Comparative Production Example 1, and a conventional resin had been each dissolved, was applied onto a glass plate, using a doctor blade (400 μm). After drying it, using a texture analyzer TAXT plus (manufactured by Eko Instruments Co., Ltd.), the properties (hardness, elasticity, and tackiness) of the coating film were evaluated under the following conditions. The results are shown in Table 1.

Tackiness measurement conditions: 25 mmϕ cylinder, trigger force of 40 g, needle penetration rate of 0.5 mm/sec, depth of 5.0 mm, and contact time of 10 sec Elasticity measurement conditions: 2 mmϕ needle, trigger force of 10 g, strain of 50%, and needle penetration rate of 0.01 mm/sec Hardness measurement conditions: 2 mmϕ needle, trigger force of 10 g, strain of 50%, and needle penetration rate of 0.5 mm/sec It is to be noted that the Tg of each resin is indicated as a Tg value calculated according to the following Fox formula:

$$1/Tg = W_1/Tg_1 + W_2/Tg_2 + \ldots + W_n/Tg_n$$

$W_1$ to $W_n$ indicate the weight fraction of an n type of monomer used in the synthesis of a base for hair cosmetics. $Tg_1$ to $Tg_n$ indicate the glass transition temperature of a homopolymer obtained by polymerization of each monomer alone. However, in the Examples of the present invention, such $Tg_1$ to $Tg_n$ indicate the glass transition temperature (Tg) theoretically calculated from only EA and HEMA.

TABLE 1

| | Tg | Hardness [g] | Elasticity [-] | Tackiness [g] |
|---|---|---|---|---|
| Production Example 2 | 20 | 30.6 | 60.6 | 310.6 |
| Production Example 9 | 11 | 12.6 | 65 | 174.3 |
| Production Example 10 | 11 | 18.2 | 35.3 | 200.3 |
| Production Example 11 | 11 | 14.8 | 35 | 174.0 |
| Production Example 12 | 10 | 17.3 | 40 | 236.9 |
| Production Example 13 | 11 | 12.7 | 31.8 | 254.8 |
| Production Example 14 | 30 | 69.2 | 16.5 | 96.2 |
| Production Example 15 | 15 | 24.3 | 48.5 | 195.8 |
| Production Example 16 | −10 | 34.1 | 10.3 | 687.6 |
| Comparative Production Example 1 | 20 | 25.7 | 50.3 | 318.9 |
| Conventional resin (Note 10) | | 109.4 | 7.7 | 98.9 |

Note 10:
Amphomer KS (manufactured by Akzo Nobel)

(2) Evaluation of Solubility

The copolymers obtained in the above described Production Examples 1 to 8 and Comparative Production Examples 1 to 4 and a commercially available styling resin (vinyl pyrrolidone/vinyl acetate copolymer; Comparative Production Example 5) were each dissolved in 99.5% ethanol under heating (70° C.), so as to obtain a solution containing 50% each copolymer. Thereafter, the turbidity of each solution was evaluated at 25° C. by visual observation. The results are shown in Table 2.

Evaluation Standard:
Excellent—dissolved transparently or semi-transparently
Poor—Not dissolved (precipitate found in lower layer)

(3) Evaluation of Elasticity

A 20% ethanol solution, in which the copolymers obtained in the above described Production Examples 1 to 8 and Comparative Production Examples 1 to 4 and a commercially available styling resin (vinyl pyrrolidone/vinyl acetate copolymer; Comparative Production Example 5) had been each dissolved, was applied onto a glass plate, using a doctor blade (400 μm). After drying it, elasticity was evaluated using a texture analyzer TAXT plus (manufactured by Eko Instruments Co., Ltd.). A certain load was applied two times, and the times required for reaching the highest value were defined as L1 and L2. Elasticity was indicated with L2/L1. The results are shown in Table 2.

Evaluation Standard:
Excellent—elasticity of 30 or more
Good—elasticity of 20 or more and less than 30
Fair—elasticity of 10 or more and less than 20
Poor—elasticity of less than 10

Elasticity correlates with "bounce and resilience" in sensory evaluation, and the elasticity that was in a good range in the above evaluation standard was also good in the bounce and resilience of hair.

(4) Evaluation of Copolymers Used as Hair Mists

1) Evaluation of Ability to Adsorb on Hair

The copolymers obtained in the above described Production Examples 1 to 8 and Comparative Production Examples 1 to 4 and a commercially available styling resin (vinyl pyrrolidone/vinyl acetate copolymer; Comparative Production Example 5) were each mixed with other components shown in Table 3 below, and according to a production method as described below, hair mists containing 0.5 mass % each copolymer were prepared.

A commercially available black hair bundle (approximately 1.0 g) was immersed in the above prepared hair mist for 1 minute, and it was then dried at a room temperature for 1 day. After completion of the drying, the mass of the dried hair bundle was measured. The results are shown in Table 2.

Evaluation Standard:
Excellent—The amount of the hair mist adhered to 1 g of hair is 25.0 mg or more.
Good—The amount adhered to 1 g of hair is 15.0 mg or more and less than 25.0 mg.
Fair—The amount adhered to 1 g of hair is 5.0 mg or more and less than 15.0 mg.
Poor—The amount adhered to 1 g of hair is less than 5.0 mg.

TABLE 2

|  | Production Example | | | | | | | | Comparative Production Example | | | | |
| --- | --- | --- | --- | --- | --- | --- | --- | --- | --- | --- | --- | --- | --- |
|  | 1 | 2 | 3 | 4 | 5 | 6 | 7 | 8 | 1 | 2 | 3 | 4 | 5 |
| Solubility in ethanol | Excellent | Excellent | Excellent | Excellent | Excellent | Excellent | Excellent | Excellent | Poor | Excellent | Excellent | Excellent | Excellent |
| Elasticity | Excellent | Excellent | Excellent | Excellent | Excellent | Excellent | Excellent | Excellent | — | Poor | Poor | Poor | Poor |
| Ability to adsorb on hair | Excellent | Excellent | Excellent | Excellent | Excellent | Excellent | Excellent | Excellent | — | Excellent | Excellent | Excellent | Poor |

2) Evaluation of Stability, Smoothness, Silky Feeling, Elasticity (Bounce and Resilience) and Non-Stickiness The hair mists prepared in (4) above were evaluated under the following evaluation standard. The results are shown in Table 3.

TABLE 3

(Mass %)

|  |  | Example | | | | | | | | Comparative Example | | | | |
| --- | --- | --- | --- | --- | --- | --- | --- | --- | --- | --- | --- | --- | --- | --- |
| No. | Component | 1 | 2 | 3 | 4 | 5 | 6 | 7 | 8 | 1 | 2 | 3 | 4 | 5 |
| 1 | Purified water | Balance | Balance | Balance | Balance | Balance | Balance | Balance | Balance | Balance | Balance | Balance | Balance | Balance |
| 3 | Ethanol | 10 | 10 | 10 | 10 | 10 | 10 | 10 | 10 | 10 | 10 | 10 | 10 | 10 |
| 4 | Propylene glycol | 1 | 1 | 1 | 1 | 1 | 1 | 1 | 1 | 1 | 1 | 1 | 1 | 1 |
| 5 | Stearyl trimethyl ammonium chloride (Note 11) | 0.5 | 0.5 | 0.5 | 0.5 | 0.5 | 0.5 | 0.5 | 0.5 | 0.5 | 0.5 | 0.5 | 0.5 | 0.5 |
| 6 | Polyoxyethylene hydrogenated castor oil isostearate | 0.2 | 0.2 | 0.2 | 0.2 | 0.2 | 0.2 | 0.2 | 0.2 | 0.2 | 0.2 | 0.2 | 0.2 | 0.2 |
| 7 | P-methoxybenzoic acid ester | 0.2 | 0.2 | 0.2 | 0.2 | 0.2 | 0.2 | 0.2 | 0.2 | 0.2 | 0.2 | 0.2 | 0.2 | 0.2 |
| 8 | Ethanol | 2 | 2 | 2 | 2 | 2 | 2 | 2 | 2 | 2 | 2 | 2 | 2 | 2 |
| 9 | Production Example 1 | 0.5 | — | — | — | — | — | — | — | — | — | — | — | — |
| 10 | Production Example 2 | — | 0.5 | — | — | — | — | — | — | — | — | — | — | — |
| 11 | Production Example 3 | — | — | 0.5 | — | — | — | — | — | — | — | — | — | — |
| 12 | Production Example 4 | — | — | — | 0.5 | — | — | — | — | — | — | — | — | — |
| 13 | Production Example 5 | — | — | — | — | 0.5 | — | — | — | — | — | — | — | — |
| 14 | Production Example 6 | — | — | — | — | — | 0.5 | — | — | — | — | — | — | — |
| 15 | Production Example 7 | — | — | — | — | — | — | 0.5 | — | — | — | — | — | — |
| 16 | Production Example 8 | — | — | — | — | — | — | — | 0.5 | — | — | — | — | — |
| 17 | Comparative Production Example 1 | — | — | — | — | — | — | — | — | 0.5 | — | — | — | — |
| 18 | Comparative Production Example 2 | — | — | — | — | — | — | — | — | — | 0.5 | — | — | — |
| 19 | Comparative Production Example 3 | — | — | — | — | — | — | — | — | — | — | 0.5 | — | — |
| 20 | Comparative Production Example 4 | — | — | — | — | — | — | — | — | — | — | — | 0.5 | — |
| 21 | (Octylacrylamide/hydroxypropyl acrylate/butylaminoethyl methacrylate) copolymer (Note 12) | — | — | — | — | — | — | — | — | — | — | — | — | 0.5 |
| 22 | Fragrance | Proper amount | Proper amount | Proper amount | Proper amount | Proper amount | Proper amount | Proper amount | Proper amount | Proper amount | Proper amount | Proper amount | Proper amount | Proper amount |

TABLE 3-continued (Mass %)

| No. Component | Example | | | | | | | | Comparative Example | | | | |
|---|---|---|---|---|---|---|---|---|---|---|---|---|---|
| | 1 | 2 | 3 | 4 | 5 | 6 | 7 | 8 | 1 | 2 | 3 | 4 | 5 |
| <Evaluation items> | | | | | | | | | | | | | |
| Stability (solubility) | Excellent | Excellent | Excellent | Good | Excellent | Excellent | Excellent | Excellent | Poor | Excellent | Excellent | Excellent | Excellent |
| Smoothness | Excellent | Excellent | Excellent | Good | Excellent | Good | Excellent | Excellent | Poor | Poor | Good | Good | Good |
| Silky feeling | Excellent | Excellent | Excellent | Excellent | Excellent | Excellent | Good | Excellent | Poor | Poor | Good | Good | Good |
| Elasticity (bounce and resilience) | Excellent | Excellent | Excellent | Excellent | Excellent | Excellent | Excellent | Excellent | Poor | Poor | Poor | Poor | Poor |
| Non-stickiness | Excellent | Excellent | Excellent | Excellent | Excellent | Excellent | Excellent | Excellent | Poor | Poor | Poor | Poor | Poor |

Note 11: GENAMINE STAC (manufactured by Clariant Japan K. K.)
Note 12: Amphomer KS (manufactured by Akzo Nobel)

Production Method

A: mixing and dissolving components 1 to 7

B: mixing and dissolving components 9 to 21 in component 8

C: adding B to A and mixing them

D: adding component 22 to C.

Evaluation Standard

Stability:

Excellent—dissolved transparently or semi-transparently

Good—Clouded

Poor—Not dissolved (precipitate found in lower layer)

"Smoothness", "silky feeling", "elasticity (bounce and resilience)", and "Non-stickiness":

Twenty panelists who were specialized for evaluation of cosmetic products were asked to use the hair mists of Examples 1 to 8 and Comparative Examples 1 to 5. Thereafter, they evaluated individual samples on a 7-point scale in accordance with the following evaluation standard, in terms of "smoothness", "silky feeling", "elasticity (bounce and resilience)", and "non-stickiness". They scored every sample. Subsequently, each product was evaluated based on an average of scores given by all of the panelists in accordance with the following criteria.

Evaluation Standard

| (Evaluation) | (Content) |
|---|---|
| 6 | Excellent |
| 5 | Good |
| 4 | Fair |
| 3 | Normal |
| 2 | Slightly poor |
| 1 | Poor |
| 0 | Extremely poor |

| Criteria (Average of scores) | (Judgment) |
|---|---|
| 5.0 or more | E (excellent) |
| 3.5 or more and less than 5.0 | G (good) |
| 1.5 or more and less than 3.5 | F (fair) |
| Less than 1.5 | P (poor) |

3 Formulation Examples of Cosmetics

Example 1

Skin Lotion

Skin lotion having the following composition was produced by the following method.

| (Components) | (%) |
|---|---|
| 1. (Meth)acrylic silicone-based graft copolymer (Production Example 1) | 0.02 |
| 2. 2-Glucoside ascorbate | 2.0 |
| 3. Citric acid | 0.01 |
| 4. Sodium monohydrogen phosphate | 0.1 |
| 5. Purified water | Balance |
| 6. Ethanol | 8.0 |
| 7. Polyoxyethylene polyoxypropylene decyl tetradecyl ether (30EO, 6PO) | 0.3 |
| 8. Phenoxyethanol | 0.1 |
| 9. Fragrance | Proper amount |

(Production Method)

(1) Components 1 to 6 were stirred homogeneously.

(2) Components 7 to 9 were added to (1), and the mixture was then stirred homogeneously, so that the components could be solubilized to obtain skin lotion.

The skin lotion of Example 1 was excellent in smooth use feeling and adhesiveness.

Example 2

Two-Layer Lotion

Two-layer lotion having the following composition was produced by the following method.

| (Components) | (%) |
|---|---|
| 1. Polyoxyethylene alkyl ether phosphate | 0.01 |
| 2. Purified water | 2.5 |
| 3. Zinc oxide | 0.5 |
| 4. Aluminum chloride | 0.1 |
| 5. Purified water | Balance |
| 6. Ethanol | 20.0 |
| 7. Polyoxyethylene hydrogenated castor oil isostearate | 0.1 |

-continued

| (Components) | (%) |
|---|---|
| 8. (Meth)acrylic silicone-based graft copolymer (Production Example 2) | 0.02 |
| 9. Methylparaben | 0.1 |
| 10. Fragrance | proper amount |

(Production Method)
(1) Components 1 to 3 were mixed.
(2) Components 4 to 10 were added to (1), and the obtained mixture was then homogeneously stirred to obtain two-layer lotion.

The two-layer lotion of Example 2 was excellent in powder dispersibility, and was also excellent in smooth use feeling and adhesiveness.

Example 3

Emulsion

Emulsion having the following composition was produced by the following method.

| (Components) | (%) |
|---|---|
| 1. Stearic acid | 0.5 |
| 2. Polyoxyethylene sorbitan monostearate (20EO) | 1.0 |
| 3. Polyoxypropylene sorbitol tetraoleate (40EO) | 1.0 |
| 4. Behenyl alcohol | 1.5 |
| 5. Liquid paraffin | 5.0 |
| 6. Glyceryl tri(2-ethylhexanoate) | 5.0 |
| 7. Methylpolysiloxane | 1.0 |
| 8. (Meth)acrylic silicone-based graft copolymer (Production Example 3) | 0.02 |
| 9. Xanthan gum | 0.1 |
| 10. 1,3-Butylene glycol | 8.0 |
| 11. Ethanol | 5.0 |
| 12. Methylparaben | 0.1 |
| 13. Sodium hydroxide | 0.07 |
| 14. Fragrance | Proper amount |
| 15. Purified water | Balance |

(Production method)
(1) Components 1 to 7 were homogeneously mixed with one another at 80° C.
(2) Components 8 to 15 were homogeneously mixed with one another at 80° C.
(3) (2) was added to (1), and the obtained mixture was then emulsified.
(4) While stirring, (3) was cooled, so as to obtain emulsion.

The emulsion of Example 3 was excellent in emulsion stability, and was also excellent in smooth use feeling and adhesiveness.

Example 4

Cream

Cream having the following composition was produced by the following method.

| (Components) | (%) |
|---|---|
| 1. Stearic acid | 1.5 |
| 2. Decaglyceryl pentaoleate | 2.5 |
| 3. Behenyl alcohol | 1.5 |

-continued

| (Components) | (%) |
|---|---|
| 4. Vaseline | 3.0 |
| 5. Heavy liquid isoparaffin | 1.0 |
| 6. Glyceryl tri(2-ethylhexanoate) | 3.0 |
| 7. Methylpolysiloxane | 1.0 |
| 8. Purified water | Balance |
| 9. Glycerin | 7.0 |
| 10. Triethanolamine | 0.3 |
| 11. Ethanol | 5.0 |
| 12. (Meth)acrylic silicone-based graft copolymer (Production Example 4) | 0.05 |
| 13. Xanthan gum | 0.2 |
| 14. Methylparaben | 0.1 |
| 15. Fragrance | Proper amount |

(Production Method)
(1) Components 1 to 7 were homogeneously mixed with one another at 80° C.
(2) Components 8 to 15 were homogeneously mixed with one another at 80° C.
(3) (1) was added to (2), and the obtained mixture was then emulsified.
(4) While stirring, (3) was cooled, so as to obtain cream.

The cream of Example 4 was excellent in emulsion stability, and was also excellent in smooth use feeling and adhesiveness.

Example 5

Beauty Essence

Beauty essence having the following composition was produced by the following method.

| (Components) | (%) |
|---|---|
| 1. Xanthan gum | 0.3 |
| 2. 1,3-Butylene glycol | 7.0 |
| 3. Glycerin | 10.0 |
| 4. (Meth)acrylic silicone-based graft copolymer (Production Example 5) | 0.02 |
| 5. Purified water | Balance |
| 6. Ethanol | 6.0 |
| 7. Wild rose extract | 0.1 |
| 8. Methylparaben | 0.1 |
| 9. Fragrance | Proper amount |

(Production Method)
(1) Components 1 to 9 were mixed and dissolved in one another at an ordinary temperature, and the mixture was then stirred, so as to obtain beauty essence.

The beauty essence of Example 5 was excellent in emulsion stability, and was also excellent in smooth use feeling and adhesiveness.

Example 6

Facial Mask

Facial mask having the following composition was produced by the following method.

| (Components) | (%) |
|---|---|
| 1. Glyceryl tri(2-ethylhexanoate) | 0.2 |
| 2. Liquid paraffin | 7.0 |

-continued

| (Components) | (%) |
| --- | --- |
| 3. Polyoxyethylene polyoxypropylene cetyl ether (20EO, 4PO) | 1.0 |
| 4. 1,3-Butylene glycol | 0.1 |
| 5. Glycerin | 10.0 |
| 6. (Meth)acrylic silicone-based graft copolymer (Production Example 6) | 0.02 |
| 7. Hydroxyethyl cellulose | 0.7 |
| 8. Purified water | Balance |
| 9. Ethanol | 6.0 |
| 10. Methylparaben | 0.1 |
| 11. Fragrance | Proper amount |

(Production Method)

(1) Components 1 to 3 were homogeneously mixed with one another at 80° C.

(2) Components 4 to 11 were homogeneously mixed with one another at 80° C.

(3) (1) was added to (2), and the obtained mixture was then emulsified.

(4) While stirring, (3) was cooled, so as to obtain facial mask.

The facial mask of Example 6 was excellent in emulsion stability, and was also excellent in smooth use feeling and adhesiveness.

Example 7

Facial Cleanser

Facial cleanser having the following composition was produced by the following method.

| (Components) | (%) |
| --- | --- |
| 1. Myristic acid | 5.0 |
| 2. Palmitic acid | 20.0 |
| 3. Stearic acid | 5.0 |
| 4. Polyethylene glycol 6000 | 3.0 |
| 5. Glycerin | 15.0 |
| 6. 1,3-Butylene glycol | 5.0 |
| 7. Ethylene glycol distearate | 1.5 |
| 8. (Meth)acrylic silicone-based graft copolymer (Production Example 6) | 0.02 |
| 9. Ethanol | 0.5 |
| 10. Potassium hydroxide | 6.0 |
| 11. Purified water | Balance |
| 12. Methylparaben | 0.1 |
| 13. Fragrance | Proper amount |

(Production Method)

(1) Components 1 to 7 were homogeneously mixed with one another at 80° C.

(2) Components 8 to 13 were homogeneously mixed with one another at 80° C.

(3) (2) was added to (1), and while stirring, the obtained mixture was cooled, so as to obtain facial cleanser.

The facial cleanser of Example 7 was excellent in foam-retaining property and water washability.

Example 8

Cleansing Gel

Cleansing gel having the following composition was produced by the following method.

| (Components) | (%) |
| --- | --- |
| 1. (Meth)acrylic silicone-based graft copolymer (Production Example 7) | 0.05 |
| 2. Hydroxypropylmethyl cellulose | 5.0 |
| 3. Purified water | Balance |
| 4. Polyoxyethylene glyceryl triisostearate (20EO) | 8.0 |
| 5. Polyoxyethylene lauryl ether (5EO) | 5.0 |
| 6. 1,3-Butylene glycol | 10.0 |
| 7. Ethanol | 5.0 |
| 8. Methylparaben | 0.1 |
| 9. Fragrance | Proper amount |

(Production Method)

(1) Components 1 to 9 were homogeneously mixed with one another at an ordinary temperature to obtain cleansing gel.

The cleansing gel of Example 8 was excellent in smooth use feeling and water washability.

Example 9

Cleansing Cream

Cleansing cream having the following composition was produced by the following method.

| (Components) | (%) |
| --- | --- |
| 1. Stearic acid | 3.0 |
| 2. Cetanol | 2.0 |
| 3. Polyoxypropylene sorbitol tetraoleate (40EO) | 1.0 |
| 4. Polyoxyethylene sorbitan monostearate (20EO) | 1.0 |
| 5. Glyceryl tri(2-ethylhexanoate) | 20.0 |
| 6. Liquid paraffin | 20.0 |
| 7. Decamethylcyclopentasiloxane | 5.0 |
| 8. (Meth)acrylic silicone-based graft copolymer (Production Example 1) | 0.1 |
| 9. Xanthan gum | 0.2 |
| 10. 1,3-Butylene glycol | 7.0 |
| 11. Ethanol | 5.0 |
| 12. Sodium hydroxide | 0.5 |
| 13. Purified water | Balance |
| 14. Methylparaben | 0.1 |
| 15. Fragrance | Proper amount |

(Production Method)

(1) Components 1 to 7 were homogeneously mixed with one another at 80° C.

(2) Components 8 to 15 were homogeneously mixed with one another at 80° C.

(3) (1) was added to (2), and the obtained mixture was then emulsified.

(4) While stirring, (3) was cooled, so as to obtain cleansing cream.

The cleansing cream of Example 9 was excellent in emulsion stability and water washability.

Example 10

Mousse-Type Hair Dressing

Mousse-type hair dressing having the following composition was produced by the following method.

| (Components) | (%) |
|---|---|
| 1. Ethanol | 5.0 |
| 2. Stearyl trimethyl ammonium chloride | 0.5 |
| 3. Purified water | Balance |
| 4. (Meth)acrylic silicone-based graft copolymer (Production Example 2) | 0.05 |
| 5. Propylene glycol | 0.5 |
| 6. Methylparaben | 0.1 |
| 7. Fragrance | Proper amount |

(Production Method)
(1) Components 1 to 7 were mixed with one another at an ordinary temperature.
(2) 100 parts of (1) were filled into an aerosol can, and 10 parts of liquefied petroleum gas was then injected into the can, so as to obtain mousse-type hair dressing.

The mousse-type hair dressing of Example 10 was excellent in hair styling property, and was also excellent in smooth use feeling.

Example 11

Spray-Type Hair Dressing

Spray-type hair dressing having the following composition was produced by the following method.

| (Components) | (%) |
|---|---|
| 1. Ethanol | Balance |
| 2. (Meth)acrylic silicone-based graft copolymer (Production Example 3) | 1.5 |
| 3. Glyceryl tri(2-ethylhexanoate) | 0.15 |
| 4. Phenoxyethanol | 0.2 |
| 5. Fragrance | Proper amount |

(Production Method)
(1) Components 1 to 5 were homogeneously mixed with one another at an ordinary temperature.
(2) 60 parts of (1) were filled into an aerosol can, and 15 parts of liquefied petroleum gas and 25 parts of dimethyl ether were then injected into the can, so as to obtain hair dressing (spray).

The spray-type hair dressing of Example 11 was excellent in hair styling property, provided smooth use feeling, and was also excellent in water washability.

Example 12

Hair Wax

Hair wax having the following composition was produced by the following method.

| (Components) | (%) |
|---|---|
| 1. Purified water | Balance |
| 2. Sodium hydroxide | 0.15 |
| 3. Propylene glycol | 10.0 |
| 4. Polyethylene glycol monostearate | 3.0 |
| 5. Stearic acid | 1.0 |
| 6. Vaseline | 10.0 |
| 7. Paraffin wax | 3.0 |
| 8. Cetostearyl alcohol | 3.0 |
| 9. Behenyl alcohol | 3.0 |
| 10. Methylpolysiloxane | 2.0 |
| 11. Ethanol | 5.0 |
| 12. Purified water | 15.0 |
| 13. (Meth)acrylic silicone-based graft copolymer (Production Example 4) | 1.0 |
| 14. Xanthan gum | 0.5 |
| 15. Methylparaben | 0.1 |
| 16. Fragrance | Proper amount |

(Production Method)
(1) Components 1 to 3 were homogeneously mixed with one another at 80° C.
(2) Components 4 to 10 were homogeneously mixed with one another at 80° C.
(3) (2) was added to (1), and the obtained mixture was then emulsified.
(4) Components 11 to 16 were added to (3), and while stirring, the obtained mixture was cooled, so as to obtain hair wax.

The hair wax of Example 12 was excellent in hair styling property, provided smooth use feeling, and was also excellent in water washability.

Example 13

Oily Eyeliner

Oily eyeliner having the following composition was produced by the following method.

| (Components) | (%) |
|---|---|
| 1. Ceresin wax | 11.0 |
| 2. Polyisobutylene | 16.0 |
| 3. Polyethylene wax | 8.0 |
| 4. Light liquid isoparaffin | Balance |
| 5. Silicone-treated black iron oxide | 15.0 |
| 6. Silicone-treated talc | 5.0 |
| 7. (Meth)acrylic silicone-based graft copolymer (Production Example 5) | 0.1 |
| 8. Methylparaben | 0.1 |
| 9. Fragrance | Proper amount |

(Production Method)
(1) Components 1 to 4 were heated to 100° C., and were then homogeneously mixed with one another.
(2) Components 5 to 9 were heated to 80° C., and were then homogeneously mixed with one another.
(3) (2) was added to (1), and the obtained mixture was then blended homogeneously.
(4) (3) was treated with a roller, so as to obtain eyeliner (oil type).

The eyeliner of Example 13 was excellent in smooth use feeling and adhesiveness.

Example 14

Aqueous Eyeliner

Aqueous eyeliner having the following composition was produced by the following method.

| (Components) | (%) |
|---|---|
| 1. 1,3-Butylene glycol | 15.0 |
| 2. Polyoxy alkyl ether phosphate | 0.2 |
| 3. Polyoxyethylene cetyl ether | 0.2 |
| 4. Black iron oxide | 15.0 |
| 5. Silicic acid anhydride | 3.0 |
| 6. Acrylic acid alkyl copolymer emulsion (Note 13) | 15.0 |
| 7. (Meth)acrylic silicone-based graft copolymer (Production Example 6) | 0.1 |
| 8. Ethanol | 2.0 |
| 9. Purified water | Balance |
| 10. Methylparaben | 0.1 |
| 11. Fragrance | Proper amount |

(Note 13)
Yodozol 32A707 (solid content: 45%) (manufactured by Nippon NSC Ltd.)

(Production Method)
(1) Components 1 to 5 were homogeneously dispersed using a roller.
(2) Components 6 to 11 were homogeneously mixed with one another.
(3) (1) was added to (2), and the obtained mixture was then blended homogeneously, so as to obtain aqueous eyeliner.

The aqueous eyeliner of Example 14 was excellent in smooth use feeling and adhesiveness.

Example 15

Eyebrow

Eyebrow having the following composition was produced by the following method.

| (Components) | (%) |
|---|---|
| 1. Acrylic acid alkyl copolymer emulsion (Note 13) | 30.0 |
| 2. (Meth)acrylic silicone-based graft copolymer (Production Example 7) | 0.5 |
| 3. L-arginine | 1.0 |
| 4. Purified water | Balance |
| 5. Ethanol | 15.0 |
| 6. Polyoxyethylene sorbitan monooleate (20EO) | 0.5 |
| 7. 1,3-Butylene glycol | 2.0 |
| 8. Black iron oxide | 0.05 |
| 9. Yellow iron oxide | 0.05 |
| 10. Colcothar | 0.25 |
| 11. Methylparaben | 0.1 |
| 12. Fragrance | Proper amount |

(Note 13)
Yodozol 32A707 (solid content: 45%) (manufactured by Nippon NSC Ltd.)

(Production Method)
(1) Components 1 to 5 were homogeneously mixed with one another.
(2) Components 6 to 10 were treated using a roller.
(3) (2) and components 11 and 12 were added to (1), and the obtained mixture was then blended homogeneously, so as to obtain eyebrow.

The eyebrow of Example 15 was excellent in smooth use feeling and adhesiveness.

Example 16

O/W Type Mascara

O/W type mascara having the following composition was produced by the following method.

| (Components) | (%) |
|---|---|
| 1. Stearic acid | 2.0 |
| 2. Beeswax | 10.0 |
| 3. Cetostearyl alcohol | 1.0 |
| 4. Polyoxyethylene sorbitan monooleate (20EO) | 1.5 |
| 5. Sorbitan sesquioleate | 0.5 |
| 6. Glyceryl tri(2-ethylhexanoate) | 5.0 |
| 7. Black iron oxide | 5.0 |
| 8. Silicic acid anhydride | 3.0 |
| 9. Purified water | Balance |
| 10. 1,3-Butylene glycol | 10.0 |
| 11. Triethanolamine | 1.5 |
| 12. Acrylic acid alkyl copolymer emulsion (Note 13) | 30.0 |
| 13. (Meth)acrylic silicone-based graft copolymer (Production Example 1) | 0.5 |
| 14. Ethanol | 1.0 |
| 15. Methylparaben | 0.1 |
| 16. Fragrance | Proper amount |

(Note 13)
Yodozol 32A707 (solid content: 45%) (manufactured by Nippon NSC Ltd.)

(Production Method)
(1) Components 1 to 3 were homogeneously mixed with one another at 80° C.
(2) Components 4 to 8 were treated using a roller.
(3) (2) was added to (1), and the obtained mixture was then blended homogeneously.
(4) Components 9 to 16 were homogeneously mixed with one another at 80° C.
(5) (3) was added to (4), and the obtained mixture was then emulsified.
(6) (5) was cooled, so as to obtain mascara (O/W).

The O/W type mascara of Example 16 was excellent in powder dispersibility and emulsion stability, and was also excellent in smooth use feeling and adhesiveness.

Example 17

Non-Aqueous Mascara

Non-aqueous mascara having the following composition was produced by the following method.

| (Components) | (%) |
|---|---|
| 1. Pentaerythrit rosinate | 10.0 |
| 2. Candelilla resin | 3.0 |
| 3. Beeswax | 2.0 |
| 4. Ceresin wax | 2.0 |
| 5. Palmitic acid dextrin | 2.0 |
| 6. Trimethylsiloxysilicic acid | 3.0 |
| 7. (Meth)acrylic silicone-based graft copolymer (Production Example 2) | 0.05 |
| 8. Dimethyl distearyl ammonium hectorite | 5.0 |
| 9. Propione carbonate | 1.0 |
| 10. Light liquid isoparaffin | Balance |
| 11. Black iron oxide | 5.0 |
| 12. Silica | 3.0 |
| 13. Talc | 5.0 |

(Production Method)
(1) Components 1 to 5 were heated to 110° C.
(2) Components 6 to 10 were added to and mixed with (1).
(3) Components 11 to 13 were added to and mixed with (2).
(4) (3) was treated using a roller, so as to obtain mascara (non-aqueous type).

The non-aqueous mascara of Example 17 was excellent in smooth use feeling and adhesiveness.

Example 18

Lipstick

Lipstick having the following composition was produced by the following method.

| (Components) | (%) |
|---|---|
| 1. Polyethylene wax | 7.0 |
| 2. Microcrystalline wax | 3.0 |
| 3. Ceresin wax | 2.0 |
| 4. Glyceryl tri(2-ethylhexanoate) | 20.0 |
| 5. Pentaerythrit tetra(2-ethylhexanoate) | 10.0 |
| 6. Dimethylpolysiloxane | 3.0 |
| 7. Cetyl 2-ethylhexanoate | Balance |
| 8. (Meth)acrylic silicone-based graft copolymer (Production Example 3) | 0.02 |
| 9. Red No. 202 | 0.5 |
| 10. Yellow No. 4 | 2.0 |
| 11. Titanium oxide | 0.5 |
| 12. Black iron oxide | 0.1 |
| 13. Phenoxyethanol | 0.2 |
| 14. Fragrance | Proper amount |

(Production Method)
(1) Components 1 to 7 were homogeneously mixed and dissolved in one another at 100° C.
(2) Components 8 to 14 were added to (1), and the obtained mixture was then blended homogeneously.
(3) (2) was poured into a vessel, and was then cooled, so as to obtain lipstick.

The lipstick of Example 18 was excellent in smooth use feeling and adhesiveness.

Example 19

O/W Type Foundation

An O/W type foundation having the following composition was produced by the following method.

| (Components) | (%) |
|---|---|
| 1. Polyoxyethylene sorbitan monooleate (20EO) | 0.5 |
| 2. Sorbitan sesquioleate | 0.5 |
| 3. 1,3-Butylene glycol | 10.0 |
| 4. Silicone-treated titanium oxide | 10.0 |
| 5. Silicone-treated colcothar | 0.4 |
| 6. Silicone-treated yellow iron oxide | 2.0 |
| 7. Silicone-treated black iron oxide | 0.1 |
| 8. Silicone-treated talc | 5.0 |
| 9. Xanthan gum | 0.3 |
| 10. (Meth)acrylic silicone-based graft copolymer (Production Example 4) | 0.1 |
| 11. Triethanolamine | 1.0 |
| 12. Purified water | Balance |
| 13. Ethanol | 2.0 |
| 14. Stearic acid | 1.5 |
| 15. Behenyl alcohol | 0.5 |
| 16. Liquid paraffin | 2.0 |
| 17. Glyceryl tri(2-ethylhexanoate) | 2.0 |

-continued

| (Components) | (%) |
|---|---|
| 18. 2-Ethylhexyl p-methoxycinnamate | 2.0 |
| 19. Vaseline | 0.5 |
| 20. Methylparaben | 0.1 |
| 21. Fragrance | Proper amount |

(Production Method)
(1) Components 1 to 8 were homogeneously dispersed using a roller.
(2) Components 9 to 13 were homogeneously mixed with one another.
(3) (1) was added to (2), and the obtained mixture was then blended homogeneously.
(4) Components 14 to 20 were mixed and dissolved in one another at 80° C.
(5) (4) was added to (3) at 80° C., and the obtained mixture was then emulsified.
(6) (5) was cooled, and component 21 was then added thereto, so as to obtain an O/W type foundation.

The O/W type foundation of Example 19 was excellent in powder dispersibility and emulsion stability, and was also excellent in smooth use feeling and adhesiveness.

Example 20

W/O Type Foundation

A W/O type foundation having the following composition was produced by the following method.

| (Components) | (%) |
|---|---|
| 1. Polyoxyethylene methylsiloxane/polyoxypropylene oleylmethylsiloxane/dimethylsiloxane copolymer (Note 14) | 2.0 |
| 2. PEG-3 dimethicone (Note 15) | 1.0 |
| 3. Dimethylpolysiloxane | 20.0 |
| 4. Silicone-treated red iron oxide | 1.0 |
| 5. Silicone-treated yellow iron oxide | 1.5 |
| 6. Silicone-treated black iron oxide | 0.5 |
| 7. Silicone-treated titanium oxide | 10.0 |
| 8. Silicone-treated talc | 5.0 |
| 9. Glyceryl tri(2-ethylhexanoate) | 10.0 |
| 10. Sorbitan sesquioleate | 0.5 |
| 11. Purified water | Balance |
| 12. (Meth)acrylic silicone-based graft copolymer (Production Example 5) | 0.1 |
| 13. 1,3-Butylene glycol | 10.0 |
| 14. Ethanol | 5.0 |
| 15. Methylparaben | 0.1 |
| 16. Fragrance | Proper amount |

(Note 14)
KF-6026 (manufactured by Shin-Etsu Chemical Co., Ltd.)
(Note 15)
KF-6015 (manufactured by Shin-Etsu Chemical Co., Ltd.)

(Production Method)
(1) Components 1 to 3 were homogeneously mixed with one another.
(2) Components 4 to 10 were homogeneously dispersed using a roller.
(3) (2) was added to (1), and the obtained mixture was then blended homogeneously.
(4) Components 11 to 16 were added to (3), and the obtained mixture was then emulsified, so as to obtain a W/O type foundation.

The W/O type foundation of Example 20 was excellent in powder dispersibility and emulsion stability, and was also excellent in smooth use feeling and adhesiveness.

Example 21

O/W Type Eye Color

O/W type eye color having the following composition was produced by the following method.

| (Components) | (%) |
|---|---|
| 1. Xanthan gum | 0.3 |
| 2. (Meth)acrylic silicone-based graft copolymer (Production Example 6) | 0.05 |
| 3. 1,3-Butylene glycol | 10.0 |
| 4. Ethanol | 5.0 |
| 5. Sodium hydroxide | 0.06 |
| 6. Purified water | Balance |
| 7. Stearic acid | 0.5 |
| 8. Liquid paraffin | 2.0 |
| 9. Dimethylpolysiloxane | 2.0 |
| 10. Polyoxyethylene sorbitan monooleate (20EO) | 0.2 |
| 11. Sorbitan sesquioleate | 0.1 |
| 12. 1,3-Butylene glycol | 10.0 |
| 13. Blue No. 404 | 0.5 |
| 14. Yellow iron oxide | 0.2 |
| 15. Mica titanium | 15.0 |
| 16. Synthetic phlogopite | 5.0 |
| 17. Methylparaben | 0.2 |
| 18. Fragrance | Proper amount |

(Production Method)

(1) Components 1 to 6 were homogeneously mixed with one another at 80° C.

(2) Components 7 to 9 were homogeneously mixed with one another at 80° C.

(3) (2) was added to (1), and the obtained mixture was then emulsified.

(4) Components 10 to 17 were homogeneously dispersed using a roller.

(5) (4) and component 18 were added to (3), so as to obtain O/W type eye color.

The O/W type eye color of Example 21 was excellent in powder dispersibility and emulsion stability, and was also excellent in smooth use feeling and adhesiveness.

Example 22

Oily Solid Foundation

An oily solid foundation having the following composition was produced by the following method.

| (Components) | (%) |
|---|---|
| 1. Talc | 15.0 |
| 2. Mica | 10.0 |
| 3. Silicone-treated titanium oxide | 15.0 |
| 4. Silicone-treated colcothar | 1.0 |
| 5. Silicone-treated yellow iron oxide | 3.0 |
| 6. Silicone-treated black iron oxide | 0.2 |
| 7. Polyethylene wax | 7.0 |
| 8. Microcrystalline wax | 6.0 |
| 9. Glyceryl tri(2-ethylhexanoate) | Balance |
| 10. Dimethylpolysiloxane | 10.0 |
| 11. Liquid paraffin | 20.0 |
| 12. Polyoxyethylene methylsiloxane/polyoxypropylene oleylmethylsiloxane/dimethylsiloxane copolymer (Note 14) | 2.0 |
| 13. (Meth)acrylic silicone-based graft copolymer (Production Example 7) | 0.05 |
| 14. Methylparaben | 0.1 |
| 15. Fragrance | Proper amount |

(Note 14)
KF-6026 (manufactured by Shin-Etsu Chemical Co., Ltd.)

(Production Method)

(1) Components 7 to 14 were dissolved in one another by heating at 90° C.

(2) Components 1 to 6 were added to (1), and the obtained mixture was then homogeneously dispersed using a roller.

(3) Component 15 was added to (2), the obtained mixture was then dissolved at 80° C., and the resultant was then filled into a gold dish, so as to obtain an oily solid foundation.

The oily solid foundation of Example 22 was excellent in powder dispersibility, and was also excellent in smooth use feeling and adhesiveness.

Example 23

Stick-Type Concealer

Stick-type concealer having the following composition was produced by the following method.

| (Components) | (%) |
|---|---|
| 1. Ceresin wax | 8.0 |
| 2. Polyethylene wax | 2.0 |
| 3. Dimethylpolysiloxane | 5.0 |
| 4. Glyceryl 2-ethylhexanoate | 5.0 |
| 5. Neopentyl glycol dioctanoate | Balance |
| 6. Silicone-treated titanium oxide | 5.0 |
| 7. Silicone-treated red iron oxide | 1.0 |
| 8. Silicone-treated yellow iron oxide | 1.5 |
| 9. Silicone-treated black iron oxide | 0.5 |
| 10. Zinc laurate | 5.0 |
| 11. (Meth)acrylic silicone-based graft copolymer (Production Example 1) | 0.1 |
| 12. Phenoxyethanol | 0.2 |
| 13. Fragrance | Proper amount |

(Production Method)

(1) Components 1 to 5 were dissolved in one another by heating at 90° C.

(2) Components 6 to 12 were added to (1), and the obtained mixture was then homogeneously dispersed using a roller.

(3) Component 13 was added to (2), the mixture was dissolved at 80° C., and the resultant was then filled into a vessel, so as to obtain stick-type concealer.

The stick-type concealer of Example 23 was excellent in powder dispersibility, and was also excellent in smooth use feeling and adhesiveness.

Example 24

Body Soap

Body soap having the following composition was produced by the following method.

| (Components) | (%) |
| --- | --- |
| 1. Lauric acid | 5.0 |
| 2. Myristic acid | 10.0 |
| 3. Palmitic acid | 3.5 |
| 4. Purified water | Balance |
| 5. Potassium hydroxide | 5.0 |
| 6. Lauryl dimethylaminoacetate betaine | 3.0 |
| 7. Coconut oil fatty acid diethanolamide | 3.0 |
| 8. Ethylene glycol distearate | 1.0 |
| 9. (Meth)acrylic silicone-based graft copolymer (Production Example 2) | 0.02 |
| 10. Ethanol | 0.5 |
| 11. Methylparaben | 0.1 |
| 12. Fragrance | Proper amount |

(Production Method)

(1) Components 1 to 3 were dissolved in one another at 80° C.

(2) Components 4 to 8 were dissolved in one another at 80° C.

(3) (2) was added to (1), and the obtained mixture was then blended by stirring.

(4) Components 9 to 12 were added to (3), and the obtained mixture was then cooled and defoamed, so as to obtain body soap.

The body soap of Example 24 was excellent in smooth use feeling and water washability.

Example 25

Body Milk

Body milk having the following composition was produced by the following method.

| (Components) | (%) |
| --- | --- |
| 1. Stearic acid | 1.0 |
| 2. Polyoxyethylene sorbitan monooleate (20EO) | 0.5 |
| 3. Sorbitan sesquioleate | 0.5 |
| 4. Behenyl alcohol | 0.5 |
| 5. Glyceryl 2-ethylhexanoate | 5.0 |
| 6. Liquid paraffin | 2.0 |
| 7. Dimethylpolysiloxane | 2.0 |
| 8. Ethanol | 10.0 |
| 9. Dipropylene glycol | 10.0 |
| 10. Purified water | Balance |
| 11. Sodium hydroxide | 0.15 |
| 12. Glycerin | 5.0 |
| 13. 1,3-Butylene glycol | 5.0 |
| 14. Ethanol | 5.0 |
| 15. Xanthan gum | 0.2 |
| 16. (Meth)acrylic silicone-based graft copolymer (Production Example 3) | 0.02 |
| 17. Methylparaben | 0.1 |
| 18. Fragrance | Proper amount |

(Production Method)

(1) Components 1 to 7 were dissolved in one another at 80° C.

(2) Components 8 to 18 were dissolved in one another at 80° C.

(3) (1) was added to (2), and the obtained mixture was then emulsified.

(4) (3) was cooled while stirring, so as to obtain body milk.

The body milk of Example 25 was excellent in emulsion stability and smooth use feeling.

Example 26

Shampoo

Shampoo having the following composition was produced by the following method.

| (Components) | (%) |
| --- | --- |
| 1. Coconut oil fatty acid methyl taurine sodium | 10.0 |
| 2. Sodium tetradecene sulfonate | 5.0 |
| 3. Coconut oil fatty acid amide propyl betaine | 5.0 |
| 4. Coconut oil fatty acid diethanolamide | 4.0 |
| 5. Sodium chloride | 0.5 |
| 6. Purified water | Balance |
| 7. Cationized cellulose | 0.1 |
| 8. (Meth)acrylic silicone-based graft copolymer (Production Example 4) | 0.05 |
| 9. Ethanol | 1.0 |
| 10. Methylparaben | 0.1 |
| 11. Fragrance | Proper amount |

(Production Method)

(1) Components 1 to 11 were homogeneously mixed with one another at an ordinary temperature, so as to obtain shampoo.

The shampoo of Example 26 was excellent in smooth use feeling and moist feeling.

Example 27

Conditioner

Conditioner having the following composition was produced by the following method.

| (Components) | (%) |
| --- | --- |
| 1. Behenyl alcohol | 2.0 |
| 2. Cetostearyl alcohol | 1.0 |
| 3. Glyceryl tri(2-ethylhexanoate) | 3.0 |
| 4. Alkyltrimethyl ammonium chloride | 1.0 |
| 5. Propylene glycol | 4.0 |
| 6. Ethanol | 3.0 |
| 7. Purified water | Balance |
| 8. Hydroxyethyl cellulose | 0.1 |
| 9. (Meth)acrylic silicone-based graft copolymer (Production Example 5) | 0.1 |
| 10. Methylparaben | 0.1 |
| 11. Fragrance | Proper amount |

(Production Method)

(1) Components 1 to 5 were homogeneously mixed with one another at 80° C.

(2) Components 6 to 11 were homogeneously mixed with one another at 80° C.

(3) (2) was added to (1), and the obtained mixture was then emulsified.
(4) While stirring, (3) was cooled, so as to obtain conditioner.

The conditioner of Example 27 was excellent in smooth use feeling and moist feeling.

Example 28

Hair Pack

Hair pack having the following composition was produced by the following method.

| (Components) | (%) |
|---|---|
| 1. Behenyl alcohol | 2.0 |
| 2. Cetostearyl alcohol | 6.0 |
| 3. Liquid paraffin | 3.0 |
| 4. Alkyltrimethyl ammonium chloride | 1.5 |
| 5. Propylene glycol | 4.0 |
| 6. Dimethylpolysiloxane (20 cs) | 1.0 |
| 7. Purified water | Balance |
| 8. Ethanol | 3.0 |
| 9. (Meth)acrylic silicone-based graft copolymer (Production Example 6) | 0.1 |
| 10. Methylparaben | 0.1 |
| 11. Fragrance | Proper amount |

(Production Method)
(1) Components 1 to 6 were homogeneously mixed with one another at 80° C.
(2) Components 7 to 11 were homogeneously mixed with one another at 80° C.
(3) (2) was added to (1), and the obtained mixture was then emulsified.
(4) While stirring, (3) was cooled, so as to obtain hair pack.

The hair pack of Example 28 was excellent in smooth use feeling and moist feeling.

Example 29

W/O Type Sunscreen

A sunscreen having the following composition was produced by the following method.

| (Components) | (%) |
|---|---|
| 1. Zinc oxide | 15.0 |
| 2. Silicone-treated titanium oxide fine particles | 5.0 |
| 3. Sorbitan sesquiisostearate | 1.0 |
| 4. Glyceryl tri(2-ethylhexanoate) | 10.0 |
| 5. 2-Ethylhexyl palmitate | 5.0 |
| 6. Decamethylcyclopentasiloxane | 10.0 |
| 7. 2-Ethylhexyl p-methoxycinnamate | 10.0 |
| 8. Methylpolysiloxane/cetylmethylpolysiloxane/poly(oxyethylene/oxypropylene)methylpolysiloxane copolymer (Note 16) | 2.0 |
| 9. Purified water | Balance |
| 10. Sodium chloride | 0.2 |
| 11. Ethanol | 5.0 |
| 12. (Meth)acrylic silicone-based graft copolymer (Production Example 7) | 0.1 |
| 13. Methylparaben | 0.1 |
| 14. Fragrance | Proper amount |

(Note 16)
ABIL EM90 (manufactured by EVONIC GOLDSCHMIDT GMBH)

(Production Method)
(1) Components 1 to 4 were homogeneously dispersed using a roller.
(2) Components 5 to 8 were added to (1), and the obtained mixture was then blended homogeneously.
(3) Components 9 to 14 were added to (2), and the obtained mixture was then emulsified, so as to obtain a W/O type sunscreen.

The W/O type sunscreen of Example 29 was excellent in powder dispersibility and emulsion stability, and was also excellent in smooth use feeling and adhesiveness.

Example 30

Makeup Base

Makeup base having the following composition was produced by the following method.

| (Components) | (%) |
|---|---|
| 1. Cetostearyl alcohol | 2.0 |
| 2. 2-Ethylhexyl p-methoxycinnamate | 5.0 |
| 3. Dimethylpolysiloxane | 5.0 |
| 4. Glyceryl tri(2-ethylhexanoate) | 5.0 |
| 5. Purified water | Balance |
| 6. N-stearoyl-N-methyl taurine sodium | 0.5 |
| 7. Xanthan gum | 0.2 |
| 8. (Meth)acrylic silicone-based graft copolymer (Production Example 1) | 0.02 |
| 9. Ethanol | 10.0 |
| 10. 1,3-Butylene glycol | 10.0 |
| 11. Methylparaben | 0.1 |
| 12. Fragrance | Proper amount |

(Production Method)
(1) Components 1 to 4 were dissolved in one another at 80° C.
(2) Components 5 to 11 were dissolved in one another at 80° C.
(3) (1) was added to (2), and the obtained mixture was then emulsified.
(4) Component 12 was added to (3), and the obtained mixture was then cooled, so as to obtain makeup base.

The base of Example 30 was excellent in emulsion stability, and was also excellent in smooth use feeling and adhesiveness.

Example 31

Face Powder

Face powder having the following composition was produced by the following method.

| (Components) | (%) |
|---|---|
| 1. Mica | 20.0 |
| 2. Talc | Balance |
| 3. Mica titanium | 10.0 |
| 4. Red No. 226 | 0.5 |
| 5. Liquid paraffin | 0.5 |
| 6. Glyceryl tri(2-ethylhexanoate) | 1.0 |
| 7. Methylparaben | 0.1 |
| 8. Fragrance | Proper amount |
| 9. Ethanol | 1.0 |
| 10. (Meth)acrylic silicone-based graft copolymer (Production Example 2) | 0.02 |

(Production Method)
(1) Components 1 to 4 and components 7 to 10 were homogeneously mixed with one another.
(2) Components 5 and 6 were added to (1), and the obtained mixture was then blended homogeneously.
(3) (2) was pulverized using a pulverizer to obtain face powder.

The face powder of Example 31 was excellent in powder dispersibility, and was also excellent in smooth use feeling and adhesiveness.

Example 32

Solid Powdery Foundation

A solid powdery foundation having the following composition was produced by the following method.

| (Components) | (%) |
|---|---|
| 1. Silicone-treated titanium oxide | 15.0 |
| 2. Talc | Balance |
| 3. Silicone-treated colcothar | 1.0 |
| 4. Silicone-treated yellow iron oxide | 3.0 |
| 5. Silicone-treated black iron oxide | 0.5 |
| 6. Mica | 20.0 |
| 7. Nylon powder | 2.0 |
| 8. Glyceryl tri(2-ethylhexanoate) | 3.0 |
| 9. Liquid paraffin | 3.0 |
| 10. 2-Ethylhexyl p-methoxycinnamate | 3.0 |
| 11. Methylparaben | 0.1 |
| 12. Fragrance | Proper amount |
| 13. Ethanol | 1.0 |
| 14. (Meth)acrylic silicone-based graft copolymer (Production Example 3) | 0.02 |

(Production Method)
(1) Components 1 to 7 and components 11 to 14 were homogeneously mixed with one another.
(2) Components 8 to 10 were added to (1), and the obtained mixture was then blended homogeneously.
(3) (2) was pulverized using a pulverizer.
(4) (3) was filled into a gold dish, so as to obtain solid powdery foundation.

The solid powdery foundation of Example 32 was excellent in powder dispersibility, and was also excellent in smooth use feeling and adhesiveness.

Example 33

Solid Powdery Cheek

Solid powdery cheek having the following composition was produced by the following method.

| (Components) | (%) |
|---|---|
| 1. Mica | 30.0 |
| 2. Talc | Balance |
| 3. Synthetic mica | 10.0 |
| 4. Red No. 226 | 0.5 |
| 5. Liquid paraffin | 4.0 |
| 6. Glyceryl tri(2-ethylhexanoate) | 4.0 |
| 7. Methylparaben | 0.1 |
| 8. Fragrance | Proper amount |
| 9. Ethanol | 1.0 |
| 10. (Meth)acrylic silicone-based graft copolymer (Production Example 4) | 0.02 |

(Production Method)
(1) Components 1 to 4 and components 7 to 10 were homogeneously mixed with one another.
(2) Components 5 and 6 were added to (1), and the obtained mixture was then blended homogeneously.
(3) (2) was pulverized using a pulverizer.
(4) (3) was filled into a gold dish, so as to obtain solid powdery cheek.

The solid powdery cheek of Example 33 was excellent in powder dispersibility, and was also excellent in smooth use feeling and adhesiveness.

Example 34

Solid Powdery Eye Shadow

Solid powdery eye shadow having the following composition was produced by the following method.

| (Components) | (%) |
|---|---|
| 1. Mica titanium | 30.0 |
| 2. Talc | Balance |
| 3. Ultramarine blue | 2.0 |
| 4. Yellow No. 401 | 0.5 |
| 5. Nylon powder | 2.0 |
| 6. Glyceryl tri(2-ethylhexanoate) | 4.0 |
| 7. Liquid paraffin | 4.0 |
| 8. Vaseline | 1.0 |
| 9. Methylparaben | 0.1 |
| 10. Fragrance | Proper amount |
| 11. Ethanol | 1.0 |
| 12. (Meth)acrylic silicone-based graft copolymer (Production Example 5) | 0.05 |

(Production Method)
(1) Components 1 to 5 and components 9 to 12 were homogeneously mixed with one another.
(2) Components 6 to 8 were added to (1), and the obtained mixture was then blended homogeneously.
(3) (2) was pulverized using a pulverizer.
(4) (3) was filled into a gold dish, so as to obtain a solid powdery foundation.

The solid powdery foundation of Example 34 was excellent in powder dispersibility, and was also excellent in smooth use feeling and adhesiveness.

The invention claimed is:

1. A (meth)acrylic silicone-based graft copolymer obtained by reacting the following radically polymerizable monomers (a), (b), (c) and (d), wherein the (meth)acrylic silicone-based graft copolymer is dissolved at a level of 50 mass % or more in 99.5% ethanol at 25° C.:

(a) a compound represented by the following general formula (I):

$$CH_2=C(R1)-C(=O)-O-R2-Si(Me)_2-(OSi(Me)_2)_m-R3 \quad (I)$$

(wherein Me represents a methyl group, R1 represents a hydrogen atom or a methyl group, R2 represents a linear or branched divalent saturated hydrocarbon group containing 1 to 10 carbon atoms, which optionally comprises one or two ether bonds, R3 represents a saturated hydrocarbon group containing 1 to 10 carbon atoms, and m represents an integer of 5 to 100);

(b) at least one selected from a compound represented by the following general formula (II):

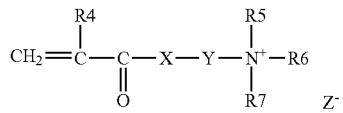

(wherein R4 represents a hydrogen atom or a methyl group, R5, R6 and R7, which are the same or different, each represent a hydrogen atom or an alkyl group containing 1 to 4 carbon atoms, X represents —O—, —NH—, —O—CH$_2$— or —O—CH$_2$CH(OH)—, Y represents a linear or branched divalent saturated hydrocarbon group containing 1 to 4 carbon atoms, and Z$^-$ represents a counter anion), and a compound represented by the following formula (III):

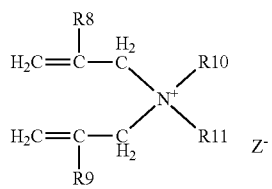

(wherein R8 and R9, which are the same or different, each represent a hydrogen atom or an alkyl group containing 1 to 4 carbon atoms, R10 and R11, which are the same or different, each represent a hydrogen atom or an alkyl group containing 1 to 18 carbon atoms, and Z$^-$ represents a counter anion);

(c) a compound represented by the following general formula (IV):

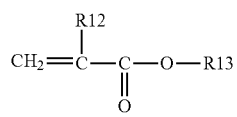

(wherein R12 represents a hydrogen atom or a methyl group, and R13 represents a hydrogen atom or a linear or branched alkyl group containing 1 to 3 carbon atoms); and (d) a compound represented by the following general formula (V):

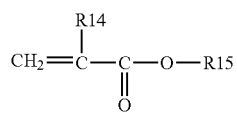

(wherein R14 represents a hydrogen atom or a methyl group, and R15 represents a hydroxyalkyl group containing 1 to 4 carbon atoms).

2. The (meth)acrylic silicone-based graft copolymer according to claim 1, which further has a repeating unit derived from a (meth)acrylic derivative other than (a) to (d).

3. The (meth)acrylic silicone-based graft copolymer according to claim 1, wherein with regard to the ratio of the monomers (a) to (d) used, (a)=20 to 50 mass %, (b)=0.5 to 4 mass %, (c) and (d)=46 to 79.5 mass %, and (c)/(d)=0.5 to 1.5.

4. The (meth)acrylic silicone-based graft copolymer according to claim 1, wherein when the copolymer is dissolved at a level of 20 mass % in 99.5% ethanol, the viscosity of the ethanol solution at 25° C. is 50 to 250 mPa·s (CS).

5. A cosmetic comprising a (meth)acrylic silicone-based graft copolymer according to any one of claims 1 to 4.

6. The cosmetic according to claim 5, which is a hair cosmetic.

* * * * *